United States Patent [19]
Yayon et al.

[11] Patent Number: 5,789,182
[45] Date of Patent: Aug. 4, 1998

[54] SYSTEM FOR ASSAYING BINDING TO A HEPARIN-BINDING GROWTH FACTOR RECEPTOR

[75] Inventors: Avner Yayon, Rehovot, Israel; David M. Ornitz, Brookline, Mass.; Michael Klagsbrun, Newton, Mass.; Philip Leder, Chestnut Hill, Mass.; John G. Flanagan, Newton, Mass.

[73] Assignees: The Children's Medical Center Corporation; President and Fellows of Harvard College, both of Boston, Mass.

[21] Appl. No.: 166,717

[22] Filed: Dec. 14, 1993

Related U.S. Application Data

[62] Division of Ser. No. 631,717, Dec. 20, 1990, Pat. No. 5,270,197.

[51] Int. Cl.$^6$ ............................. C12Q 1/00; C12N 15/09
[52] U.S. Cl. ......................... 435/721; 435/697; 435/325; 530/350; 530/402
[58] Field of Search ........................... 435/4, 7.1, 240.2, 435/325, 7.21, 69.7; 530/395, 402

[56] References Cited

U.S. PATENT DOCUMENTS

| | | | |
|---|---|---|---|
| 4,703,004 | 10/1987 | Hopp et al. | 435/68 |
| 4,882,275 | 11/1989 | Klagsbrun | 435/68 |

OTHER PUBLICATIONS

Bergonzoni et al., Characterization of a biologically active extracellular domain of fibroblast growth factor receptor 1 expressed in *Escherichia coli*, Eur. J. Biochem, 210, 823–829 (1992).

Sambrook et al., Molecular Cloning, Second Edition, vol. 3, p. 16.3, 1989, Cold Spring Harbor Laboratory Press.

Flanagan, et al. "The kit ligand: a cell surface molecule altered in steel mutant fibroblasts"Cell, 63:185–194 (1990).

Azizkhan et al., Mast Cell Heparin Stimulates Migration of Capillary Endothelial Cells In Vitro, J. Exp. Med. 152:931–944, 1980.

Baird et al., Receptor-and Heparin-binding Domains of Basic Fibroblast Growth Factor, Proc. Natl. Acad. Sci. USA 85:2324–2328, 1988.

Bashkin et al., Basic Fibroblast Growth Factor Binds to Subendothelial Extracellular Matrix and is Released by Heparitinase and Heparin–like Molecules, Biochemistry 28L1737–1743, 1989.

Dietrich et al., Cell Recognition and Adhesiveness: A Possible Biological Role for the Sulfated Mucopolysaccharides, Biochemical and Biophysical Research Communications 75:329–336, 1977.

Dionne et al., Cloning and Expression of Two Distinct High-affinity Receptors Cross-reacting with Acidic and Basic Fibroblast Growth Factors, EMBO J. 9:2685–2692, 1990.

Esko et al., Tumor Formation Dependent on Proteoglycan Biosynthesis, Science 241:1092–1096, 1988.

Folkman et al., A Heparin-binding Angiogenic Protein—Basic Fibroblast Growth Factor—Is Stored within Basement Membrane, American Journal of Pathology 130:393–400, 1988.

Folkman et al., Angiogenic Factors, Science 235:442–447, 1987.

Gordon et al., Extracellular Matrix Heparan Sulfate Proteoglycans Modulate the Mitogenic Capacity of Acidic Fibroblast Growth Factor, J. Cellular Physiology 140:584–592, 1989.

Gospodarowicz and Cheng, Heparin Protects Basic and Acidic FGF from Inactivation, J. Cellular Physiology 128:475–484, 1986.

Kaner et al., Fibroblast Growth Factor Receptor is a Portal of Cellular Entry for Herpes Simplex Virus Type 1, Science 248:1410–1413, 1990.

Klagsbrun, The Fibroblast Growth Factor Family: Structural and Biological Properties, Progress in Growth Factor Research 1:207–235, 1989.

Klagsbrun and Shing, Heparin Affinity of Anionic and Cationic Capillary Endothelial Cell Growth Factors: Analysis ... Growth Factors and Fibroblast Growth Factors, Proc. Natl. Acad. Sci. USA 82:805–809, 1985.

Kornbluth et al., Novel Tyrosine Kinase Identified by Phosphotyrosine Antibody Screening of cDNA Libraries, Molecular and Cellular Biology 8:5541–5544, 1988.

Lee et al., Purification and Complementary DNA Cloning of a Receptor for Basic Fibroblast Growth Factor, Science 245:57–60, 1989.

Mansukhani et al., A Murine Fibroblast Growth Factor (FGF) Receptor Expressed in CHO Cells is Activated by Basic FGF and Kaposi FGF, Proc. Natl. Acad. Sci. USA 87:4378–4382, 1990.

Moscatelli, Metabolism of Receptor–bound and Matrix–bound Basic Fibroblast Growth Factor by Bovine Capillary Endothelial Cells, J. Cell Biology 107:753–759, 1988.

Moscatelli, High and Low Affinity Binding Sites for Basic Fibroblast Growth Factor on Cultured Cells: Absence ... Activator Production by Bovine Capillary Endothelial Cells, J. Cell. Physiology 131:123–130, 1987.

Mueller et al., Stabilization by Heparin of Acidic Fibroblast Growth Factor Mitogenicity for Human Endothelial Cells In Vitro, J. Cellular Physiology 140:439–448, 1989.

Neufeld and Gospodarowicz, Basic and Acidic Fibroblast Growth Factors Interact with the Same Cell Surface Receptors, J. Biol. Chem. 261:5631–5637, 1986.

(List continued on next page.)

*Primary Examiner*—Sally P. Teng
*Attorney, Agent, or Firm*—Clark & Elbing LLP

[57] ABSTRACT

A homogeneous population of cells having on average (1) a number of cell surface low-affinity heparin-binding growth factor (HBGF) sites per cell less than 20% of the number of such binding sites found on wild-type CHO-K1 cells (ATCC Accession No. CCL61), and at least three times the number of cell surface high-affinity HBGF receptors per cell found on such CHO-K1 cells; and an assay system utilizing such cells.

28 Claims, 24 Drawing Sheets

OTHER PUBLICATIONS

Pasquale and Singer et al., Identification of a Developmentally Regulated Protein-tyrosine Kinase by Using Anti-phosphotyrosine Antibodies . . . cDNA Expression Library, Proc. Natl. Acad. Sci. USA 86:5449–5453, 1989.

Rifkin and Moscatelli, Recent Developments in the Cell Biology of Basic Fibroblast Growth Factor, J. Cell Biology 109:1–6, 1989.

Ruta et al., A Novel Protein Tyrosine Kinase Gene Whose Expression is Modulated During Endothelial Cell Differentiation, Oncogene 3:9–15, 1988.

Safran et al., The Murine flg Gene Encodes a Receptor for Fibroblast Growth Factor, Oncogene 5:635–43, 1990.

Saksela et al., Endothelial Cell-derived Heparan Sulfate Binds Basic Fibroblast Growth Factor and Protects it from Proteolytic Degradation, J. Cell Biology 107:743–751, 1988.

Seno et al., Carboxyl-terminal Structure of Basic Fibroblast Growth Factor Significantly Constributes to its Affinity for Heparin, Eur. J. Biochem. 188:239–245, 1990.

Shing et al., Heparin Affinity: Purification of a Tumor-derived Capillary Endothelial Cell Growth Factor, Science 223:1296–1299, 1984.

Taylor and Folkman, Protamine is an Inhibitor of Angiogenesis, Nature 297:307–312, 1982.

Thornton et al., Human Endothelial Cells: Use of Heparin in Cloning and Long-term Serial Cultivation, pp. 623–625, 1983.

Vlodavsky et al., Endothelial Cell-derived Basic Fibroblast Growth Factor: Synthesis and Deposition into Subendothelial Extracellular Matrix, Proc. Natl. Acad. Sci. USA 84:2292–2296, 1987.

WuDunn and Spear, Initial Interaction of Herpes Simplex Virus with Cells is Binding to Heparan Sulfate, J. Virology 63:52–58, 1989.

Yayon et al., Cell Surface, Heparin-like Molecules are Required for Binding of Basic Fibroblast Growth Factor to its High Affnity Receptor, Cell 64:941–848, 1991.

```
  1  MWGWKCLLFW  AVLVTATLCT  ARPAPTLPEQ  AQPWGVPVEV  ESLLVHPGDL
 51  LQLRCRLRDD  VQSINWLXDG  VQLVESNRTR  ITGEEVEVRD  SIPADSGLYA
101  CVTSSPSGSD  TTYFSVNVSD  ALPSSEDDDD  DDDSSSEEKE  TDNTKPNPVA
151  PYWTSPEKME  KKLHRVPAAK  TVKFKCPSSG  TPNPTLRWLK  NGKEFKPDHR
201  IGGYKVRYAT  WSIIMDSVVP  SDKGNYTCIV  ENEYGSINHT  YQLDVVERSP
251  HRPILQAGLX  ANKTVALGSN  VEFMCKVYSD  PXPHIQWLKH  IEVNGSKIGP
301  DNLPYVQILK  TAGVNTTDKE  MEVLHLRNVS  FEDAGEYTCL  AGNSIGLSHH
351  SAWLTVLEAL  EERPAVMTSP  LYLEIIYCT   GAFLISCMLG  SVIIYKMKSG
401  TKKSDFHSQM  AVHKLAKSIP  LRRQVTVSAD  SSASMNSGVL  LVRPSRLSSS
451  GTPMLAGVSE  YELPEDPRWE  LPRDRLVLGK  PLGEGCFGQV  VLAEAIGLDK
501  DKPNRVTKVA  VKMLKSDATE  KDLSDLISEM  EMMKMIGKHK  NIINLLGACT
551  QDGPLYVIVE  YASKGNLREY  LQARRPPGLE  YCYNPSHNPE  EQLSSKDLVS
601  CAYQVARGME  YLASKKCIHR  DLAARNVLVT  EDNVMKIADF  GLARDIHHID
651  YYKKTTNGRL  PVKWMAPEAL  FDRIYTHQSD  VWSFGVLLWE  IFTLGGSPYP
701  GXPVEELFKL  LKEGHRMDKP  SNCTNELYMM  MRDCWHAVPS  QRPTFKQLVE
751  DLDRIVALTS  NQEYLDLSIP  LDQYSPSFPD  TRSSTCSSGE  DSVFSHEPLP
801  EEPCLPRHPT  QLANSGLKRR  *
```

FIG. 9A

```
            E
  E         H         Ac   H
  c         AaSX      BhoNBa
  o         vemm      aa7abe              G
  R         aIaa      nI8reI              s
  I         IIII      IIIIII              u
                                          I
  /         / /       / /
  GGAATTCGGCACGAGCGCCCGGGCTGGAGGCGCCCGGCTCGGAGTGCCGCCGGGAGTCGT
1 ---------+---------+---------+---------+---------+---------+ 60
  CCTTAAGCCGTGCTCGCGGGCCCGACCTCCGCGGGCCGAGCCTCACGGCGGCCCTCAGCA

N   S   A   R   A   P   G   L   E   A   P   G   S   E   C   R   R   E   S   C -

B                                      B
                                s                                      s
        X   N       E   p                                              p
        Gm  sS      c   B  1                    X   A                  B1
        CdaD pa     o   aA2SX                   h   l                  a2
        fiIs Bc     3   nv8ch                   o   w                  n8
        rIIa II     1   Ia6io                   I   N                  I6
        IIII II     I   IIIII                   I   I                  II
        //          /   / /                                            /
  GCCTCGGCCGCGGAGCCCTCGAGACCCCATCAGGATCTGAACGGAGCCCGGAGACGAGCG
61 ---------+---------+---------+---------+---------+---------+ 120
  CGGAGCCGGCGCCTCGGGAGCTCTGGGGTAGTCCTAGACTTGCCTCGGGCCTCTGCTCGC

L   G   R   G   A   L   E   T   P   S   G   S   E   R   S   P   E   T   S   G -

G   D
                                    s   s
                                    u   a
                                    I   I
  GCGGGAcGCAAGACACAGACACCCSCCSCGCCACGgACAGCTCTCCAGAGGCGGGACCGC
121 ---------+---------+---------+---------+---------+---------+ 180
  CGCCCTgCGTTCTGTGTCTGTGGGSGGSGCGGTGCcTGTCGAGAGGTCTCCGCCCTGGCG

G   T   Q   D   T   D   T   ?   ?   A   T   D   S   S   P   E   A   G   P   O -

H                                                      DNS
        a                                                      sct
        e                                                      aoy
        I                                                      III
        I                                                      //
  AGCGCCAAGTGAGAGTCAGCTTGCGAAGGCAGACCACGCTCACGGTGGAaTATCCATGGA
181 ---------+---------+---------+---------+---------+---------+ 240
  TCGCGGTTCACTCTCAGTCGAACGCTTCCGTCTGGTGCGAGTGCCACCTtATAGGTACCT

R   Q   V   R   V   S   L   R   R   Q   T   T   L   T   V   E   Y   P   W   R -

GGTACGGAGCCTTGTTACCAACCTCTAACCGCAGAACTGGGATGTGGGGCTGGAAGTGCC
241 ---------+---------+---------+---------+---------+---------+ 300
  CCATGCCTCGGAACAATGGTTGGAGATTGGCGTCTTGACCCTACACCCCGACCTTCACGG
```

FIG. 9B

```
              Y   G   A   L   L   P       S   N   R   R   T   G   M   W   G   W   K   C   L  -
                      K
                      s
                      p
                      6
                      3                                           H
                      2                                           a
                      I                                           e
                                                                  I
      TCCTCTTCTGGGCTGTGCTGGTCACAGCCACTCTCTGCACTGCCAGGCCAGCCCCAACCT
301   ---------+---------+---------+---------+---------+---------+ 360
      AGGAGAAGACCCGACACGACCAGTGTCGGTGAGAGACGTGACGGTCCGGTCGGGGTTGGA

L   F   W   A   V   L   V   T   A   T   L   C   T   A   R   P   A   P   T   L  -
                          E
                          s
                          p
                          I
      TGCCCGAACAAGCTCAGCCCTGGGGAGTCCCTGTGGAAGTGGAGTCTCTCCTGGTCCACC
361   ---------+---------+---------+---------+---------+---------+ 420
      ACGGGCTTGTTCGAGTCGGGACCCCTCAGGGACACCTTCACCTCAGAGAGGACCAGGTGG

P   E   Q   A   Q   P   W   G   V   P   V   E   V   E   S   L   L   V   H   P  -
                              B
                              s                       N
                              p                       r
                              M                       u
                              I                       I
      CTGGCGACCTGCTACAGCTTCGCTGTCGGCTTCGCGATGATGTGCAGAGCATCAACTGGC
421   ---------+---------+---------+---------+---------+---------+ 480
      GACCGCTGGACGATGTCGAAGCGACAGCCGAAGCGCTACTACACGTCTCGTAGTTGACCG

G   D   L   L   Q   L   R   C   R   L   R   D   D   V   Q   S   I   N   W   L  -
                                  N
                                  sP
                                  pv
                                  Bu
                                  II
                                  II
                                  /
      TksGGGATGGGGTGCAGCTGGTGGAGAGCAACCGTACCCGCATCACAGGGGAGGAGGTGG
481   ---------+---------+---------+---------+---------+---------+ 540
      AmsCCCTACCCCACGTCGACCACCTCTCGTTGGCATGGGCGTAGTGTCCCCTCCTCCACC

?   D   G   V   Q   L   V   E   S   N   R   T   R   I   T   G   E   E   V   E  -
                              N
                              s
                              p                           H
                              B                           a
                              I                           e
                                                          I
      AGGTGCGGGACTCCATCCCCGCTGACTCTGGCCTCTACGCTTGCGTGACCAGCAGCCCCT
541   ---------+---------+---------+---------+---------+---------+ 600
      TCCACGCCCTGAGGTAGGGGCGACTGAGACCGGAGATGCGAACGCACTGGTCGTCGGGGA

```
     CTGGCAGCGATACCACCTACTTCTCCGTCAATGTCTCAGATGCACTCCCATCCTCGGAAG
601  ------------+---------+---------+---------+---------+---------+ 660
     GACCGTCGCTATGGTGGATGAAGAGGCAGTTACAGAGTCTACGTGACTGTAGGAGCCTTC

G  S  D  T  T  Y  F  S  V  N  V  S  D  A  L  P  S  S  E  D -

ATGATGACGACGACGATGACTCCTCCTCGGAGGAGAAAGAGACGGACAACACCAAACCAA
661  ------------+---------+---------+---------+---------+---------+ 720
     TACTACTGCTGCTGCTACTGAGGAGGAGCCTCCTCTTTCTCTGCCTGTTGTGGTTTGGTT

D  D  D  D  D  D  S  S  E  E  K  E  T  D  N  T  K  P  N -
                                                              B
                                                              a
                                                              n
                                                              I
     ACCCTGTAGCTCCCTACTGGACATCCCCAGAGAAAATGGAGAAGAAACTGCATCGGGTGC
721  ------------+---------+---------+---------+---------+---------+ 780
     TGGGACATCGAGGGATGACCTGTAGGGGTCTCTTTTACCTCTTCTTTGACGTAGCCCACG

P  V  A  P  Y  W  T  S  P  E  K  M  E  K  K  L  H  R  V  P -

B                            B
     s                            s
     p  N                         p                               T
     1  s                         1                               a
     2  p                         2                               q
     8  B                         8                               I
     6  I                         6                               I
     I  I
     CCGCTGCCAAGACGGTGAAGTTCAAGTGCCCGTCGAGTGGGACACCCAACCCCACTCTGC
781  ------------+---------+---------+---------+---------+---------+ 840
     GGCGACGGTTCTGCCACTTCAAGTTCACGGGCAGCTCACCCTGTGGGTTGGGGTGAGACG

A  A  K  T  V  K  F  K  C  P  S  S  G  T  P  N  P  T  L  R

B
                                           s
                                           t
                                           X
                                           I
     GCTGGTTGAAAAATGGCAAAGAGTTTAAGCCTGACCACCGAATTGGAGGCTACAAGGTTC
841  ------------+---------+---------+---------+---------+---------+ 900
     CGACCAACTTTTTACCGTTTCTCAAATTCGGACTGGTGGCTTAACCTCCGATGTTCCAAG

W  L  K  N  G  K  E  F  K  P  D  H  R  I  G  G  Y  K  V  R -

G  B
                                       s  a
                                       u  n
                                       1  I
     GCTATGCCACCTGGAGCATCATAATGGATTCTGTGGTGCCTTCTGACAAGGGCAACTACA
901  ------------+---------+---------+---------+---------+---------+ 960
     CGATACGGTGGACCTCGTAGTATTACCTAAGACACCACGGAAGACTGTTCCCGTTGATGT

Y  A  T  W  S  I  I  M  D  S  V  V  P  S  D  K  G  N  Y  T

B                                                    A  A
        s                                                    h  a
        p                                                    a  t
        M                                                    I  I
        I                                                    I  I
     CCTGCATCGTGGAGAATGAGTATGGGAGCATCAACCACACCTACCAGCTTGACGTCGTGG
961  ------------+---------+---------+---------+---------+---------+ 1020
     GGACGTAGCACCTCTTACTCATACCCTCGTAGTTGGTGTGGATGGTCGAACTGCAGCACC
```

FIG. 9D

```
           C   I   V   E   N   E   Y   G   S   I   N   H   T   Y   Q   L   D   V   V   E
                           E
                           c
                           o
                           5
                           7
                           I
       AACGATCTCCGCACCGACCCATCCTTCAGGCAGGGCTGSCTGCCAACAAGACAGTGGCCC
1021   ---------+---------+---------+---------+---------+---------+ 1080
       TTGCTAGAGGCGTGGCTGGGTAGGAAGTCCGTCCCGACSGACGGTTGTTCTGTCACCGGG

R   S   P   H   R   P   I   L   Q   A   G   L   ?   A   N   K   T   V   A   L -

TGGGCAGCAATGTGGAGTTCATGTGTAAGGTGTACAGCGATCCsmAGCCTCACATTCAGT
1081   ---------+---------+---------+---------+---------+---------+ 1140
       ACCCGTCGTTACACCTCAAGTACACATTCCACATGTCGCTAGGskTCGGAGTGTAAGTCA

G   S   N   V   E   F   M   C   K   V   Y   S   D   P   ?   P   H   I   Q   W -

E
       A                           c
       l                           o
       w                           5
       N                           7
       I                           I
       GGCTGAAGCACATCGAGGTGAACGGGAGTAAGATCGGGCCAGACAACTTGCCGTATGTCC
1141   ---------+---------+---------+---------+---------+---------+ 1200
       CCGACTTCGTGTAGCTCCACTTGCCCTCATTCTAGCCCGGTCTGTTGAACGGCATACAGG

L   K   H   I   E   V   N   G   S   K   I   G   P   D   N   L   P   Y   V   Q -

E
       X   A           B           c
       h   l           b           o                   G
       o   w           v           5                   s
       I   N           I           7                   u
       I   I           I           I                   I
       AGATCCTGAAGACTGCTGGAGTTAATACCACCGACAAGGAAATGGAGGTGCTTCATCTAC
1201   ---------+---------+---------+---------+---------+---------+ 1260
       TCTAGGACTTCTGACGACCTCAATTATGGTGGCTGTTCCTTTACCTCCACGAAGTAGATG

I   L   K   T   A   G   V   N   T   T   D   K   E   M   E   V   L   H   L   R -

T
                                       t
                                       h
                                       1
                                       1       A X
                                       1       c c
                                       1       c a
                                       I       I I
       GGAATGTCTCCTTTGAGGATGCGGGGGAGTATACGTGCTTGGCGGGTAACTCTATCGGAC
1261   ---------+---------+---------+---------+---------+---------+ 1320
       CCTTACAGAGGAAACTCCTACGCCCCCTCATATGCACGAACCGCCCATTGAGATAGCCTG

```
      TCTCCCATCACTCTGCATGGTTGACCGTTCTGGAAGCCCTGGAAGAGAGACCAGCTGTGA
1321  ---------+---------+---------+---------+---------+---------+  1380
      AGAGGGTAGTGAGACGTACCAACTGGCAAGACCTTCGGGACCTTCTGTCTGGTCGACACT

S  H  H  S  A  W  L  T  V  L  E  A  L  E  E  R  P  A  V  M  -

D
                                           G  r     P
                                           s  a     s
                                           u  I     I
                                           I  I     I
      TGACCTCACCGCTCTACCTGGAGATCATTATCTACTGCACCGGGGCCTTCCTGATCTCCT
1381  ---------+---------+---------+---------+---------+---------+  1440
      ACTGGAGTGGCGAGATGGACCTCTAGTAATAGATGACGTGGCCCCGGAAGGACTAGAGGA

T  S  P  L  Y  L  E  I  I  I  Y  C  T  G  A  F  L  I  S  C  -
                           374
                        B
                        s
                        p              K              K
                   N    B1             s              s
                   s    a2             p              p
                   p    n8             6      B       6
                   H    16             3      a       3
                   I    II             2      n       2
                                       I      I       I
                        /
      GCATGTTGGGCTCTGTCATCATCTATAAGATGAAGAGCGGCACCAAGAAGAGCGACTTCC
1441  ---------+---------+---------+---------+---------+---------+  1500
      CGTACAACCCGAGACAGTAGTAGATATTCTACTTCTCGCCGTGGTTCTTCTCGCTGAAGG

M  L  G  S  V  I  I  Y  K  M  K  S  G  T  K  K  S  D  F  H  -

B
                           s
                           p
                    A      1H
                    p      2g     C    BH              F       G
                    a      8i     f    aa              s       s
                    L      6A     r    le              p       u
                    I      II     I    II              I       I
                           /           /
      ATAGCCAGATGGCTGTGCACAAGCTGGCCAAGAGCATCCCTCTGCGCAGACAGGTAACAG
1501  ---------+---------+---------+---------+---------+---------+  1560
      TATCGGTCTACCGACACGTGTTCGACCGGTTCTCGTAGGGAGACGCGTCTGTCCATTGTC

S  Q  M  A  V  H  K  L  A  K  S  I  P  L  R  R  Q  V  T  V  -

N
              sP
              pv
              Bu                                        G       B
              II                                        s       u
              II                                        u       I
                                                        I       I
              /
      TGTCAGCTGACTCCAGTGCATCCATGAACTCTGGGGTTCTCCTGGTTCGGCCCTCACGGC
1561  ---------+---------+---------+---------+---------+---------+  1620
      ACAGTCGACTGAGGTCACGTAGGTACTTGAGACCCCAAGAGGACCAAGCCGGGAGTGCCG

S  A  D  S  S  A  S  M  N  S  G  V  L  L  V  R  P  S  R  L  -

B
                                                        s
              N                                         p
              s    DP                                   B1   H   BX
              p    rp  P                                a2GAgS   ah
              B    au  s                                n8soia   mo
```

FIG. 9F

```
             I  IM  s                              I6UcAc HI
             I  II  I                              IIIIII II
                /                                  // // /
      TCTCCTCCAGCGGGACCCCCATGCTGGCTGGAGTCTCCGAATATGAGCTCCCTGAGGATC
1621  --------+---------+---------+---------+---------+---------+ 1680
      AGAGGAGGTCGCCCTGGGGGTACGACCGACCTCAGAGGCTTATACTCGAGGGACTCCTAG

S   S   S   G   T   P   M   L   A   G   V   S   E   Y   E   L   P   E   D   P  -

N
              s
              p                                                                B
              B                                                                s
              I                                                                p
              I                                                                M
                                                                               I
      CCCGCTGGGAGCTGCCACGAGACAGACTGGTCTTAGGCAAACCACTTGGCGAGGGCTGCT
1681  --------+---------+---------+---------+---------+---------+ 1740
      GGGCGACCCTCGACGGTGCTCTGTCTGACCAGAATCCGTTTGGTGAACCGCTCCCGACGA

R   W   E   L   P   R   D   R   L   V   L   G   K   P   L   G   E   G   C   F  -

B
                                  H           s
                                  a           t
                                  e           X
                                  I           I
      TCGGGCAGGTGGTGTTGGCTGAGGCCATCGGGCTGGATAAGGACAAACCCAACCGTGTGA
1741  --------+---------+---------+---------+---------+---------+ 1800
      AGCCCGTCCACCACAACCGACTCCGGTAGCCCGACCTATTCCTGTTTGGGTTGGCACACT

G   Q   V   V   L   A   E   A   I   G   L   D   K   D   K   P   N   R   V   T  -

G
               Cd                                 DP        X
               fi                M                rp   P    Mh
               rI                m                au   s    mo
               II                e                IM   s    eI
                /                I                II   I    II
                                                    /
      CCAAAGTGGCCGTGAAGATGTTGAAGTCCGACGCAACGGAGAAGGACCTGTCGGATCTGA
1801  --------+---------+---------+---------+---------+---------+ 1860
      GGTTTCACCGGCACTTCTACAACTTCAGGCTGCGTTGCCTCTTCCTGGACAGCCTAGACT

K   V   A   V   K   M   L   K   S   D   A   T   E   K   D   L   S   D   L   I  -

TCTCGGAGATGGAGATGATGAAAATGATTGGGAAGCACAAGAATATCATCAACCTTCTGG
1861  --------+---------+---------+---------+---------+---------+ 1920
      AGAGCCTCTACCTCTACTACTTTTACTAACCCTTCGTGTTCTTATAGTAGTTGGAAGACC

S   E   M   E   M   M   K   M   I   G   K   H   K   N   I   I   N   L   L   G  -

B
                        s
                        p
                A       1H
                p       2g
                a       8i
                L       6A
                I       II
                         /
      GAGCGTGCACACAGGATGGTCCTCTTTATGTCATTGTGGAGTACGCCTCCAAAGGCAATC
1921  --------+---------+---------+---------+---------+---------+ 1980
      CTCGCACGTGTGTCCTACCAGGAGAAATACAGTAACACCTCATGCGGAGGTTTCCGTTAG

```
                                                      c                 s
                                                      a                 u
                                                      I                 I
     TCCGGGAGTATCTACAGGCCCGGAGGNCTCCTGGGCTGGAGTACTGCTATAACCCCAGCC
1981 ------------+---------+---------+---------+---------+---------+ 2040
     AGGCCCTCATAGATGTCCGGGCCTCCNGAGGACCCGACCTCATGACGATATTGGGGTCGG

R    E    Y    L    Q    A    R    R    ?    P    G    L    E    Y    C    Y    N    P    S    H   -

N
                 B      sP            BX   B
           A     b      pv            gh   s                                       A
           v     v      Bu            lo   t                                       v
           a     I      II            II   X                                       a
           I     I      II            II   I                                       I
                                     /                                            
     ACAACCCCGAGGAACAGCTGTCTTCCAAAGATCTGGTATCCTGTGCCTATCAGGTGGCTC
2041 ------------+---------+---------+---------+---------+---------+ 2100
     TGTTGGGGCTCCTTGTCGACAGAAGGTTTCTAGACCATAGGACACGGATAGTCCACCGAG

N    P    E    E    Q    L    S    S    K    D    L    V    S    C    A    Y    Q    V    A    R   -

E
                                              c
                                              AXo
                                              cc3
                                              cal
                                              III
     GGGGCATGGAGTATCTTGCCTCTAAGAAGTGTATACACCGAGACCTGGCTGCTAGGAACG
2101 ------------+---------+---------+---------+---------+---------+ 2160
     CCCCGTACCTCATAGAACGGAGATTCTTCACATATGTGGCTCTGGACCGACGATCCTTGC G    M    E    Y    L    A    S    K    K    C    I    H    R    D    L    A    A    R    N    V   -

B
         s
         t                T                                       E         AXS
         E                a                                       s         vhc
         I                q                                       p         aoi
         I                I                                       I         III
                                                                           /
     TCCTGGTGACCGAGGATAACGTAATGAAGATCGCAGACTTTGGCTTAGCTCGAGACATTC
2161 ------------+---------+---------+---------+---------+---------+ 2220
     AGGACCACTGGCTCCTATTGCATTACTTCTAGCGTCTGAAACCGAATCGAGCTCTGTAAG L    V    T    E    D    N    V    M    K    I    A    D    F    G    L    A    R    D    I    H   -

T
                                                                            t
                              CX                                            h
                              GEm                                           I
                              CdraN                                         I
                              fiIIa                                         I
                              rIOIe                                         I
                              IIIII
                             / /
     ATCATATCGACTACTACAAGAAAACCACCAACGGCCGGCTGCCTGTGAAGTGGATGGCCC
2221 ------------+---------+---------+---------+---------+---------+ 2280
     TAGTATAGCTGATGATGTTCTTTTGGTGGTTGCCGGCCGACGGACACTTCACCTACCGGG H    I    D    Y    Y    K    K    T    T    N    G    R    L    P    V    K    W    M    A    P   -

```
       I I                      I
       CTGAGGCGTTGTTTGACCG TCTACACACACCAGAGCGATGTGTGGTCTTTTGGAGTGC
2281   ---------+---------+---------+---------+---------+---------+ 2340
       GACTCCGCAACAAACTGGCCTAGATGTGTGTGGTCTCGCTACACACCAGAAAACCTCACG

E  A  L  F  D  R  I  Y  T  H  Q  S  D  V  W  S  F  G  V  L -

B
       s
       p
       1H         BXT
       2g         gha
       8i         loq
       6A         III
       II         III
        /          /
       TCTTGTGGGAGATCTTCACTCTGGGTGGCTCCCCATACCCCGGTSTGCCTGTGGAGGAAC
2341   ---------+---------+---------+---------+---------+---------+ 2400
       AGAACACCCTCTAGAAGTGAGACCCACCGAGGGGTATGGGGCCASACGGACACCTCCTTG

L  W  E  I  F  T  L  G  G  S  P  Y  P  G  ?  P  V  E  E  L -

E
                                      c                 A
                                      o                 l
                                      5                 w
                                      7                 N
                                      I                 I
       TTTTCAAGCTGCTGAAGGAGGGTCATCGAATGGACAAGCCCAGTAACTGTACCAATGAGC
2401   ---------+---------+---------+---------+---------+---------+ 2460
       AAAAGTTCGACGACTTCCTCCCAGTAGCTTACCTGTTCGGGTCATTGACATGGTTACTCG

F  K  L  L  K  E  G  H  R  M  D  K  P  S  N  C  T  N  E  L -

B
                                            s
                                            pE
                               N            1c
                               sS           2o
                               pp           83
                               Hh           61
                               II           II
                                /
       TGTACATGATGATGCGCGACTGCTGGCATGCAGTGCCCTCTCAGAGACCTACGTTCAAGC
2461   ---------+---------+---------+---------+---------+---------+ 2520
       ACATGTACTACTACGCGCTGACGACCGTACGTCACGGGAGAGTCTCTGGATGCAAGTTCG

Y  M  M  M  R  D  C  W  H  A  V  P  S  Q  R  P  T  F  K  Q -

T
                  t
                  h
                  1        B
                  1        b
                  1        v                 H
                  I        I                 a
                  I        I                 e
                                             I
       AGTTGGTGGAAGACCTGGACCGCATTGTGGCCTTGACCTCCAACCAGGAGTATCTGGACC
2521   ---------+---------+---------+---------+---------+---------+ 2580
       TCAACCACCTTCTGGACCTGGCGTAACACCGGAACTGGAGGTTGGTCCTCATAGACCTGG

```
                Bs                              T           Bin
        M       sp                              a           a2gS
        m       tB              C               q           n8ia
        e       XI              a               I           I6Ac
        I       II              I               I           IIII
                 /                                           ///
        TGTCCATACCGCTGGACCAGTACTCACCCAGCTTTCCCGACACACGGAGCTCCACCTGCT
2581    ---------+---------+---------+---------+---------+---------+  2640
        ACAGGTATGGCGACCTGGTCATGAGTGGGTCGAAAGGGCTGTGTGCCTCGAGGTGGACGA

S  I  P  L  D  Q  Y  S  P  S  F  P  D  T  R  S  S  T  C  S -

B
                        T                                       s
                        t                                       p
                B       h               B                       B1
        As      b       l               s               A       a2
        op      v       l               p               o       n8
        cM      I       I               H               c       I6
        II      I       I               I               I       II
                                                                 /
        CCTCAGGGGAGGACTCTGTCTTCTCTCATGAGCCGTTACCTGAGGAGCCCTGTCTGCCTC
2641    ---------+---------+---------+---------+---------+---------+  2700
        GGAGTCCCCTCCTGAGACAGAAGAGAGTACTCGGCAATGGACTCCTCGGGACAGACGGAG

S  G  E  D  S  V  F  S  H  E  P  L  P  E  E  P  C  L  P  R -

T                       H
                                a                       a
                                q                       e
                                I                       I
                                I                       I
        GACACCCCACCCAGCTTGCCAACAGTGGACTCAAACGGCGCTGACTACCAACCCTGTCCC
2701    ---------+---------+---------+---------+---------+---------+  2760
        CTGTGGGGTGGGTCGAACGGTTGTCACCTGAGTTTGCCGCGACTGATGGTTGGGACAGGG

H  P  T  Q  L  A  N  S  G  L  K  R  R  *  L  P  T  L  S  P -

B
                                s
                                p
                                1
                                2M                              T
                                8m                              a
                                6e                              q
                                II                              I
                                                                I
        CAGTTTTCTCCCATTCCGTCGTCACCCGTGCCCCTCACCCACAATCCCCTTGTTGGACAC
2761    ---------+---------+---------+---------+---------+---------+  2820
        GTCAAAAGAGGGTAAGGCAGCAGTGGGCACGGGGAGTGGGTGTTAGGGGAACAACCTGTG

V  F  S  H  S  V  V  T  R  A  P  H  P  Q  S  P  C  W  T  H

A       E
                                                l       c               HS
                                        H       w       o               at
                                        a       N       N               eu
                                        e       I       I               II
                                        I                                /
        ACTGCCTTTCTCCTCCTCCTTTTcgCGCTGGSAAGAGgCcAGTGCCTGACTGAGGCCTTC
2821    ---------+---------+---------+---------+---------+---------+  2880
        TGACGGAAAGAGGAGGAGGAAAagcGCGACCSTTCTCCgGgTCACGGACTGACTCCGGAAG

```
                                                         p           p
                                                         6           6
                                                                     3
                                                         2           2
                                                         I           I
       CTGTGTTGTGGGCCTTCCCCCTCCATCACCCCCAAGACCCCTCTTCTCCCTCTTCTTAGC
2881   ---------+---------+---------+---------+---------+---------+ 2940
       GACACAACACCCGGAAGGGGGAGGTAGTGGGGGTTCTGGGGAGAAGAGGGAGAAGAATCG

V   L   W   A   F   P   L   H   H   P   Q   D   P   S   S   P   S   S   *   P -

T
                                 t
                                 h
                            B    l                          X
                            s    l                          Gm
                            p    l                          Cda     M
                            M    I                          fiI     m
                            I    I                          rII     e
                                                            III     I
                                                               //
       CTGCTGTGTGAGAGAGGAGCCAAGAGGCAGGTGCTTGCCGACGGCCGCATCCTCCTTCCC
2941   ---------+---------+---------+---------+---------+---------+ 3000
       GACGACACACTCTCTCCTCGGTTCTCCGTCCACGAACGGCTGCCGGCGTAGGAGGAAGGG

A   V   *   E   R   S   Q   E   A   G   A   C   R   R   P   H   P   P   S   Q -

T
                                     t
                                N    h
                                s    l
            P                   p    l
            f                   B    l
            l                   I    I
            M                   I    I
            I
       AGGTGTTGGACCAAGACCCGSCCCGCTGCCTGGCACTGCTTGGAGGTGTGCAGAGCGGAA
3001   ---------+---------+---------+---------+---------+---------+ 3060
       TCCACAACCTGGTTCTGGGCSGGGCGACGGACCGTGACGAACCTCCACACGTCTCGCCTT

V   L   D   Q   D   P   ?   R   C   L   A   L   L   G   G   V   Q   S   G   S -

H
                                              i
                          B                   n
                          s                   c
                          m                   I
                          I                   I
       GCAAGTGGAGSATCCGGGGCATTCCTGTTGACCCATCAGCCCCTTCTGTTCTGGCGGcAG
3061   ---------+---------+---------+---------+---------+---------+ 3120
       CGTTCACCTCSTAGGCCCCGTAAGGACAACTGGGTAGTCGGGGAAGACAAGACCGCCgTC

K   W   P   I   R   G   I   P   V   D   P   S   A   P   S   V   L   A   A   G -

B
                            s
                            p
          D                 Bl
          r     PS          a2                         HS          G
          a     st          n8                         at          s
          I     sy          I6                         eu          u
          I     II          II                         II          I
                /           /                           /
       GGGCCTTGGGGCTCCTGGAAGCCGTGAGGTTTCTGTTTAGGCCTTACCGAAGGCAaCCTC
3121   ---------+---------+---------+---------+---------+---------+ 3180
       CCCGGAACCCCGAGGACCTTCGGCACTCCAAAGACAAATCCGGAATGGCTTCCGTtGGAG

```
              A
              s
         B    p
         s    7B   K
         t    1a   p
         X    8n   n
         I    II   I
                /
      TGCTCCAGATGGATGGTACCAGTAGCTTCTTAATTCCAATACTAATTTGCTTTGCTGACC
3181  ---------+---------+---------+---------+---------+---------+  3240
      ACGAGGTCTACCTACCATGGTCATCGAAGAATTAAGGTTATGATTAAACGAAACGACTGG

L  Q  M  D  G  T  S  S  F  L  I  P  I  L  I  C  F  A  D  Q  -

B
              A                                              s
              s                                              p
              p  B                B         A                l
              7Bs   K              b         l                2S
              1ap   p              v         w                8t
              8nM   n              I         N                6y
              III   I                                         II
               //                                              /
      AAATACCTGCCTGGTACCAGAAGACAGGGAGGCAGAGACTGGGAGCCGTGATGTGCCCTT
3241  ---------+---------+---------+---------+---------+---------+· 3300
      TTTATGGACGGACCATGGTCTTCTGTCCCTCCGTCTCTGACCCTCGGCACTACACGGGAA

I  P  A  W  Y  Q  K  T  G  R  Q  R  L  G  A  V  M  C  P  W  -

B            B
                     s            s
                     p            p                       D
                     B1           B1                      r
              E      a2           a2                      a
              s      n8           n8                      I
              p      I6           I6                      I
              I      II           II                      I
                      /            /
      GGgCTGAGCCCTAGACTTGGGGCTCTGTACATAGCTATGAAGAAAAACACAAAGTGTATA
3301  ---------+---------+---------+---------+---------+---------+  3360
      CCcGACTCGGGATCTGAACCCCGAGACATGTATCGATACTTCTTTTTGTGTTTCACATAT

A  E  P  *  T  W  G  S  V  H  S  Y  E  E  K  H  K  V  Y  K  -

A
                        f    N
                        l    s        D
                        I    p        r            DNS
                        I    H        a            sct
                        I    I        I            apy
                                                   [1I
                                                    //
      AATCTTGAGTATATATTTACATGTCTTTTTAAAAGGGTCGTTACTAGAGATTTACCATG
3361  ---------+---------+---------+---------+---------+---------+  3420
      TTAGAACTCATATATAAATGTACAGAAAAATTTTTCCCAGCAATGATCTCTAAATGGTAC

S  *  V  Y  I  Y  M  S  F  *  K  G  S  L  L  E  I  Y  H  G  -

A
              h
              a
              I
              I
      GGGGAGACGCCCAGGGTAGCATCCGTTGCTATATATTAAAAACAAACGAACAGAAAAAAA
3421  ---------+---------+---------+---------+---------+---------+  3480
      CCCCTCTGCGGGTCCCATCGTAGGCAACGATATATAATTTTTGTTTGCTTGTCTTTTTTT
```

FIG. 9L

```
         G  D  A  Q  G  S  I  R  C  Y  I  L  K  T  N  E  Q  K  K  K  -
                        AXS
                        vhc
                        aoi
                        III
                         /
        AAAAAAAAAAAAAAACTCGAGGGGGGG
  3481  ---------+---------+-----  3503
        TTTTTTTTTTTTTTGAGCTCCCCCCC
         K  K  K  L  E  G  G  -
```

Enzymes that do cut:

| AatII   | AccI    | AflIII   | AhaII   | AlwNI   | AocI    | ApaLI   | Asp718I |
|---------|---------|----------|---------|---------|---------|---------|---------|
| AvaI    | BalI    | BamHI    | BanI    | BanII   | BbeI    | BbvII   | BglI    |
| BglII   | BsmI    | Bsp1286I | BspHI   | BspMI   | BstEII  | BstXI   | CfrI    |
| Cfr10I  | DraI    | DraII    | DraIII  | DsaI    | Eco31I  | Eco57I  | Eco78I  |
| EcoNI   | EcoRI   | EspI     | FspI    | GdiII   | GsuI    | HaeI    | HaeII   |
| HgiAI   | HincII  | KpnI     | Ksp632I | MmeI    | NaeI    | NarI    | NcoI    |
| NruI    | NspBII  | NspHI    | PflMI   | PpuMI   | PssI    | PvuII   | SacI    |
| SacII   | ScaI    | ScII     | SmaI    | SphI    | StuI    | StyI    | TaqII   |
| Tth111I | Tth111II| XcaI     | XhoI    | XhoII   | XmaI    | XmaIII  |         |

Enzymes that do not cut:

| AflII  | ApaI    | Asp700I | AsuII    | AvrII   | BclI   | BspMII | BssHII |
|--------|---------|---------|----------|---------|--------|--------|--------|
| ClaI   | Eco47III| EcoRV   | HgiEII   | HindIII | HpaI   | MfeI   | MluI   |
| NdeI   | NheI    | NotI    | NsiI     | PmaCI   | PstI   | PvuI   | RsrII  |
| SalI   | SfiI    | SnaBI   | SpeI     | SplI    | SspI   | VspI   | XbaI   |

FIG. 9M

SYSTEM FOR ASSAYING BINDING TO A HEPARIN-BINDING GROWTH FACTOR RECEPTOR

This a divisional of application Ser. No. 07/631,717, filed Dec. 20, 1990, U.S. Pat. No. 5,270,197.

BACKGROUND OF THE INVENTION

The field of the invention is heparin-binding growth factors (HBGFs). This work was supported in part by a grant from the U.S. goverment, which has certain rights in the invention.

The HBGFs are a family of mammalian growth factors related by sequence homology, receptor affinity, and, as their name implies, the ability to bind heparin. Heparin is a glycosaminoglycan (GAG) with anticoagulant activity commercially isolated from mammalian tissues as a heterogeneous mixture of variably sulfated polysaccharide chains (molecular weight 6–30 kDa) composed of repeating units of D-glucosamine and either L-iduronic acid or D-glucuronic acid. Binding to heparin has been shown to stabilize at lease some of the HBGFs against heat denaturation and proteolytic degradation (Gospodarowicz and Chen, J. Cell Physiol. 128:475–484, 1986; Saskela et al., J. Cell. Biol. 107:743–751, 1988).

Members of the HBGF family which have been identified to date include acidic fibroblast growth factor (aFGF), basic FGF (bFGF), int2 and HST (both of which are considered to be oncogenes expressed at abnormally high rates in certain cancers), K-FGF (first seen in a Kaposi's sarcoma), FGF-5, FGF-6, and keratinocyte growth factor (KGF) (Rubin et al., Proc. Natl. Acad. Sci. USA 86:802–806, 1989; Folkman and Klaqsbrun, Science 235:442–447, 1987; Klagsbrun, Progress in Growth Factor Research 1:207–235, 1989). The HBGFs stimulate proliferation, migration and differentiation of cells of mesenchymal and neuroectodermal origin. bFGF, one of the more thoroughly studied HBGFs, participates as an autocrine modulator of cell growth and transformation and is a potent angiogenic factor abundant in normal and malignantly transformed cells (Rifkin and Moscatelli, J. Cell. Biol. 109:1–6, 1989; Yayon and Klagsbrun, Proc. Natl. Acad. Sci. USA 87:5346–5350, 1990). The strong affinity of bFGF for heparin has greatly facilitated the purification and characterization of this growth factor (Shing et al., Science 223:1296–1299, 1984; Klagsbrun and Shing, Proc. Natl. Acad. Sci. USA 82:805–809, 1985). Heparin is also a potent modulator of the biological activity of bFGF and aFGF: e.g., heparin has been found to potentiate the mitogenic effect of aFGF on endothelial cells (Thornton et al., Science 222:623–625, 1983). Protamine, a protein that binds avidly to heparin, inhibits the ability of heparin to stimulate endothelial cell migration (Azizkhan et al., J. Exp. Med. 152:931–944, 1980) and inhibits angiogenesis associated with embryogenesis and inflammation (Taylor and Folkman, Nature 297:307–312, 1982).

The biological response of cells to the HBGFs is mediated through specific, high-affinity ($Kd=2-20\times10^{-11}M$) cell surface receptors which possess intrinsic tyrosine kinase activity and are phosphorylated upon binding of an HBGF (Coughlin et al., J. Biol. Chem. 263:988–933, 1988). Several closely related glycoproteins from various species have been denominated FGF receptors: these include the chicken FGF receptor (CEK) and the protein encoded by the human cDNA clone flg, as well as others (Lee et al., Science 245:57–60, 1989; Ruta et al., Oncogene 5:635–643, 1989; Kornbluth et al., Mol. and Cell. Biol. 8:5541–5544, 1988; Pasquale et al., Proc. Natl. Acad. Sci. USA 86:5449–5433, 1990; Safran et al., Oncogene 5:635–643, 1990). A lower-affinity ($Kd=10^{-7}-10^{-9}M$), large-capacity class of binding sites has also been identified (Moscatelli, J. Cell Biol. 131:123–130, 1987). These low-affinity binding sites are heparin sulfate proteoglycans (HSPGs; a class of protein-linked polysaccharides with a sugar structure similar to heparin, but having more N-acetyl groups and fewer O- and N-sulfate groups than does heparin) found on the cell surface (Moscatelli, J. Cell Biol. 107:753–759, 1988) and in the extra-cellular matrix (Vlodavsky et al., Proc. Natl. Acad. Sci. USA 84:2292–2296, 1987). bFGF can be released from these low-affinity binding sites by an excess of heparin or by enzymatic digestion with heparinases, but not with closely related GAGs such as chondroitin sulfate or by enzymes such as chondroitinase or hyaluronidase (Moscatelli, J. Cell Biol. 107:753–759, 1988; Bashkin et al., Biochem. 28:1737–1743, 1989). Recently, it has been shown that herpes simplex viruses, which are capable of binding to cell surface HSPG (WuDunn and Spear, J. Virol. 63:52–58, 1989), use the high-affinity FGF receptor as a portal of entry into cells (Kaner et al., Science 248:1410–1413, 1990).

SUMMARY OF THE INVENTION

The invention is based upon the discovery that cell surface HSPGs participate as obligatory accessory receptors to permit binding of bFGF to the high-affinity FGF receptors, and that soluble heparin or heparin-like molecules can effectively replace cell surface HSPG in this role. Such an obligatory cooperative interaction of low- and high-affinity FGF receptors represents a novel mechanism for growth factor/receptor interaction and regulation. Recognition of the crucial role of HSPG in FGF-receptor interactions, and of the fact that heparin and heparin-like molecules can substitute for cell-surface HSPG, has led to the design of two types of assays, a cell-based assay and a cell-free assay, intended to screen specifically for substances capable of affecting this trimolecular interaction. The cell-free assay of the invention provides the additional advantage of obviating the need for using cultured cells to assay for such substances, substituting instead a simpler, faster, and inherently more reproducible in vitro method.

The invention features cells (typically in the form of a homogeneous population of cells, such as a clone) having on average (1) a number of cell surface low-affinity HBGF-binding sites per cell less than 20% (and preferably 10% or less) of the number of such binding sites found on wild-type CHO-K1 cells [which are available from the American Type Culture Collection (ATCC, Bethesda, Md.) as Accession No. CCL61], and (2) at least two, and preferably three (and more preferably four or more) times the number of cell surface high-affinity HBGF receptors per cell found on such CHO-K1 cells. The high-affinity HBGF receptors expressed on the surfaces of the cells may be naturally endogenous to such cells or arise as the result of a mutation, or may be expressed from a recombinant nucleic acid on a vector either transiently transfected into the cells or incorporated into the genome of each of the cells. Such a nucleic acid may encode a homologous (i.e., derived from the same species as that of the cell) or heterologous (i.e., derived from a species different from that of the cell) high-affinity HBGF receptor. Species in which high-affinity HBGF receptors have been identified and cloned include human, chicken and mouse; it is likely that every species of vertebrate (and possibly invertebrates) will be found to have HBGFs and high-affinity HBGF receptors. Such HBGFs and high-affinity HBGF receptors can be identified and cloned by taking advantage of expected sequence homologies, using methods analogous to those described below. A number of different HBGFs (e.g., aFGF, bFGF, int2, HST, K-FGF, FGF-5, FGF-6, and KGF) have been identified, and it is likely that others exist. Many if not all of those tested, including HBGFs from several species, appear to bind to the same high-affinity receptor proteins: thus, a cell of the invention expressing one type of high-affinity HBGF receptor (e.g., an aFGF or a bFGF receptor) may be useful for assays involving a number of different HBGFs.

Given the characteristic affinity of the HBGFs for heparin, it is expected that each HBGF requires heparin or a heparin-like molecule in order to form an affinity complex with a high-affinity HBGF receptor. By heparin-like molecule is meant a polysaccharide capable of substituting for heparin in permitting the binding of an HBGF to a high-affinity HBGF receptor in any one of the assays of the invention. Molecules which have been demonstrated to be "heparin-like" molecules by this definition include highly-sulfated lung-derived heparin sulfate and a 12-sugar heparin fragment (prepared as described by Bashkin et al., Biochemistry 28:1737–1743, 1989). In contrast, under-sulfated, kidney-derived heparin sulfate and a shark cartilage-derived chondroitin sulfate (both purchased from Seikagaku Kogio Co., Tokyo, Japan) did not stimulate the binding of an HBGF to a high-affinity HBGF receptor in an assay of the invention, and thus do not qualify as "heparin-like" molecules. Whether or not a given polysaccharide qualifies as a "heparin-like" molecule can be readily determined by comparison with heparin in the assays described below. It would be expected that polysaccharides capable of releasing HBGFs from subendothelial cell matrix in a manner similar to that of heparin (Bashkin et al., Biochem 28:1737–1743, 1989) would be likely candidates for "heparin-like" molecules.

The cell of the invention may be used as a test cell in a system for assaying the ability of a substance to bind to a high-affinity HBGF receptor, which system also includes an amount of heparin (or a heparin-like molecule) sufficient to induce binding of a HBGF to a high-affinity HBGF on the test cell. The assay would include the steps of combining the substance to be tested with (a) heparin or a heparin-like molecule, and (b) a test cell, and measuring the amount of the substance that binds to high-affinity receptors on the test cell.

The cell of the invention could also be used as a test cell in a system for assaying the ability of a substance to affect the interaction between a given type of HBGF and a high-affinity HBGF receptor, which system would also include the given type of HBGF. The assay would include the steps of combining a first test cell with the given HBGF in the presence of the substance; combining a second test cell with the given HBGF in the absence of the substance; and comparing the amount of the given HBGF bound to the first cell with the amount of the given HBGF bound to the second cell.

Alternatively, each of the above-described methods and assay systems can utilize, instead of the cell of the invention, a molecule including a HBGF-binding portion of a high-affinity HBGF receptor polypeptide, or a hybrid molecule in which a HBGF-binding portion of a high-affinity HBGF receptor polypeptide is covalently linked to an antigenic moiety (a moiety such as a polypeptide which can form an immune complex with an appropriate antibody). The antigenic moiety portion of the hybrid molecule serves as a convenient means of separating bound HBGF from unbound HBGF: only that HBGF which is bound to the hybrid molecule (presumably via the high-affinity HBGF receptor-derived portion of the hybrid molecule) will be immunoprecipitated (or otherwise separated from the assay mixture) with an antibody specific for the antigenic portion of the hybrid molecule.

Also within the invention is a method of separating or isolating an HBGF from a sample (e.g., a biological fluid such as blood or serum), which method includes the steps of (1) providing an affinity compound in which a HBGF-binding portion of a high-affinity HBGF receptor protein is bound to a matrix material, (2) contacting the sample with the affinity compound in the presence of heparin or a heparin-like material to permit formation of affinity complexes between the HBGF and the affinity compound, and (3) separating the affinity complexes from the remainder of the sample. This can be conveniently accomplished if the affinity compound is packed within a column to form an affinity column over which the sample is passed.

Other features and advantages of the invention will be apparent from the following detailed description, and from the claims.

DETAILED DESCRIPTION

The drawings are first described.

BRIEF DESCRIPTION OF THE DRAWINGS

FIG. 9 is a representation of the nucleotide sequence (SEQ ID NO.:1) encoding the cloned murine bFGF receptor, and the amino acid sequence (SEQ ID NO.:6) deduced therefrom.

THE ASSAY SYSTEMS OF THE INVENTION

Each of the assay systems of the invention provides a convenient means to test various substances for their ability to interfere with or augment the HBGF/HSPG/high-affinity receptor trimolecular binding interaction. A substance which proves able to interfere significantly with this binding interaction would potentially be useful as an antitumor agent: by inhibiting the HBGF's binding to its high-affinity receptor, stimulation by the HBGF of both tumor cell growth and the angiogenesis necessary to ensure nourishment to the growing tumor is halted, and the tumor's growth curtailed. On the other hand, a substance which augments the trimolecular binding interaction would have potential applications as a promoter of beneficial regrowth of tissues, as in wound healing.

The Cell-Based Assay

The cell-based assay system of the invention utilizes cells which express on their surfaces a substantial number of high-affinity HBGF receptors, but relatively few (if any) low-affinity HBGF binding sites. Such cells may be naturally-occurring cells isolated, e.g., from a natural tissue or from a cultured cell line, or may be cells bearing a mutational defect which causes them to express little if any HSPGs on their surfaces. The cells may naturally express one or more types of high-affinity HBGF receptors, or may be stably or transiently transfected with vectors encoding one or more high-affinity receptors. In the experiments described in Example 1 below, a clone of CHO K1 cells mutationally deficient in cell-surface HSPGs and having a naturally low level of high-affinity HBGF receptors was transfected with a vector encoding the mouse high-affinity bFGF receptor, yielding both a transiently-transfected and a stably-transfected cell line which express the high-affinity bFGF receptor at the cell surface. The usefulness of other cell isolates or cell lines in the assay system of the invention can be determined by the methods described in Example 1.

The cell-based assay system of the invention can be used to assay for substances capable of interfering with or augmenting the HBGF/heparin/high-affinity HBGF receptor trimolecular binding interaction. Standard conditions for such an assay might include 100–200pM $^{125}$I-bFGF and 100 ng/ml heparin, added to a plate of confluent mutant CHO K1 cells expressing the recombinant receptor on their surfaces. Alternatively, the cell-based assay system of the invention can be used to assay for substances capable of replacing heparin or HBGF in the trimolecular binding interaction. In such an assay, a plate of confluent cells of the invention would be supplied with, e.g., 100–200 pM $^{125}$I-bFGF and either heparin or the substance of interest in a range of concentrations. The amount of $^{125}$I bound to the high-affinity receptors on the cells could be analyzed by, for example, the methods described in Example 1 below.

The Cell-Free Assay

Figure 10:
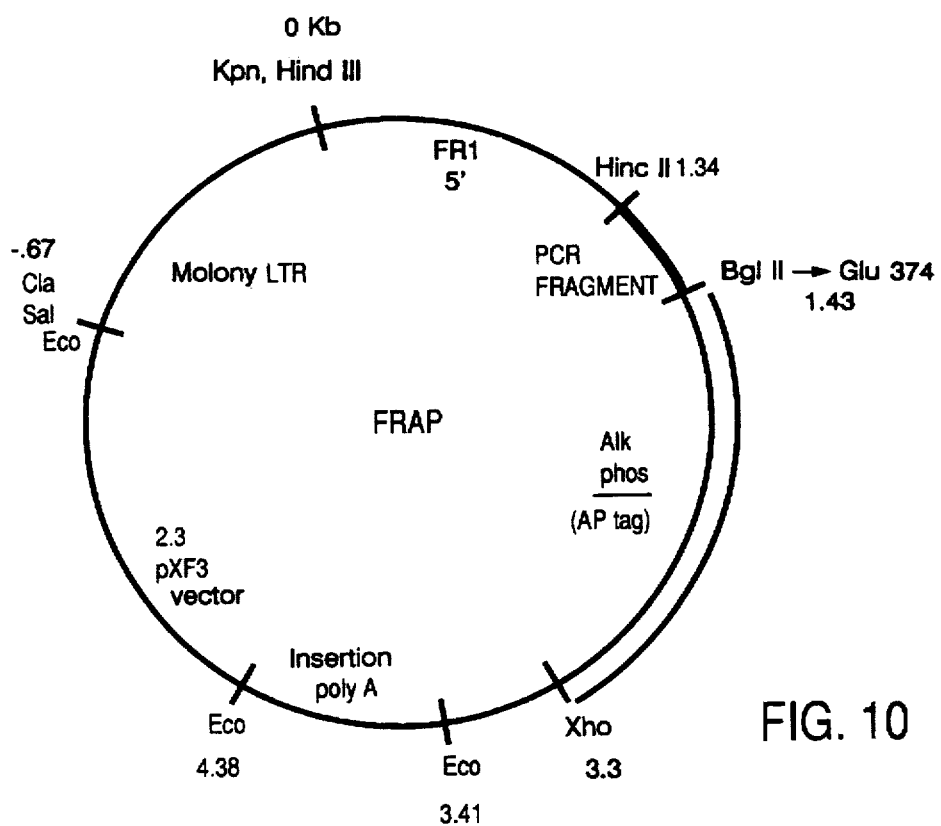
FIG. 10 is a schematic diagram of the FRAP plasmid, indicating the locations of certain restriction sites.

The cell-free assay of the invention utilizes the HBGF-binding portion of a HBGF high-affinity receptor protein to assay for substances which can affect, or replace heparin or HBGF in, the trimolecular interaction. In the experiments described in Example 2 below, a recombinant fusion protein consisting of the portion of the murine bFGF high-affinity receptor protein which is on the amino-terminal side of the cell-membrane-spanning domain (as evidenced by the predominantly hydrophobic amino acid sequence of the latter domain) linked to alkaline phosphatase was expressed from an appropriately-constructed vector, and was found to bind labelled bFGF in the presence but not in the absence of heparin or a heparin-like molecule. Alkaline phosphatase was made a part of the hybrid protein because it simplified screening for and purifying the hybrid protein; other enzymes and/or antigens could readily substitute for alkaline phosphatase, or it could be dispensed with entirely and, with appropriate screening and purification modifications, solely the HBGF-binding portion of a HBGF high-affinity receptor used in the cell-free assay of the invention. Any portion of the HBGF high-affinity receptor protein can be utilized so long as it binds HBGF in the presence and not in the absence of heparin or a heparin-like molecule, and so long as it can be expressed as a cell-free, soluble protein (i.e., lacking most or all of the cell-membrane-spanning hydrophobic domain (amino acid residues 375–395 of the intact mouse bFGF high-affinity receptor protein, the sequence of which is shown in FIG. 10). Such portions of the HBGF high-affinity receptor protein can be produced by well-known techniques of deletion mapping or polymerase chain reaction (PCR) mutagenesis, and then tested for their usefulness in the cell-free assay system of the invention by comparison with the fusion protein described in Example 2, using appropriate modifications of the assay methods described therein.

Experimental Information

Described in detail below are the cell-based system of the invention (Example 1) and the cell-free system of the invention (Example 2).

EXAMPLE 1

Cell-based System

Experimental Procedures

Materials

Recombinant human bFGF was a gift from Takeda Inc., Tokyo, Japan. Heparin was obtained from Hepar, Franklin, Ohio. Shark cartilage-derived chondroitin sulfate and undersulfated, kidney-derived heparin sulfate (HS) were purchased from Seikagaku Kogio Co., Tokyo, Japan. A twelve-sugar heparin fragment and a highly-sulfated, lung-derived HS were kindly provided by Dr. Vlodavsky, Hadassah Medical School, Jerusalem, Israel. Heparinase was a generous gift of Ibex Technologies, Montreal, Canada.

Cloning the Murine FGF Receptor

Sequence comparison of the mouse BEK cDNA (mBEK, Kornbluth et al., Mol. and Cell Biol. 8:5541–5544, 1988), the human FLG cDNA (hFLG, Ruta et al., Oncogene 3:9–15, 1988), and the chicken FGF receptor cDNA (CEK1, Pasquale and Singer, Proc. Natl. Acad. Sci. USA 86:5449–5533, 1989) was used to design a pair of PCR primers corresponding to regions highly conserved among the three species. The 5' primer of the pair is GGAGATCTC-CCATCACTCTGCATGGTTG (SEQ ID NO.: 3). The 3' 22 nucleotides of this primer are identical to a 22-nucleotide sequence of both CEK1 (beginning at position 1091 of CEK1, 86 bp 5' to the transmembrane domain of CEK) and hFLG. The 3' primer is CCGAATTCATCTTCATCATCTC-CATCTC (SEQ ID NO.: 5). The 3' 22 nucleotides of this primer are identical to a second 22-nucleotide sequence of CEK1 (beginning at position 1665 of CEK1), and contain only one mismatch to corresponding 22-nucleotide portions of hFLG and mBEK. These primers were used to amplify a 574 bp fragment from mouse liver and seminal vesicle first strand CDNA (prepared using a Boehringer Mannheim Biochemicals CDNA synthesis kit). The amplified PCR fragments were subcloned into pGEM7Zf (Promega). Sequence comparison between this PCR clone and CEK1, hFLG and MBEK revealed 84%, 90%, and 74% sequence identity, respectively, consistent with this clone's representing the mouse homologue of the FGF receptor gene, and mBEK's being a closely related cDNA. We refer to this 574 bp probe and subsequent clones as mFR, for "mouse FGF receptor". This probe was then used to screen 300,000 plaques from a murine Balb/c cDNA library in Lambda ZAP (Stratagene, La Jolla, CA). Twelve of approximately 100 hybridizing plaques were examined. One of these contained a 3.5 kb insert which, by sequence comparison to CEK1, was determined to encode a full-length FGF receptor with approximately 84% nucleotide identity to CEK1 over the open reading frame. Sequence comparison of mFR (the sequence of which is shown in FIG. 9) and a subsequently-published murine FGF receptor (Reid et al., Proc. Natl. Acad. Sci. USA 87:1596–1600, 1990) revealed nearly 100% identity: mFR contains the 5' 267 bp domain and is missing the six nucleotides coding for amino acids 148 and 149, variants also observed by Reid et al.

Figure 2:
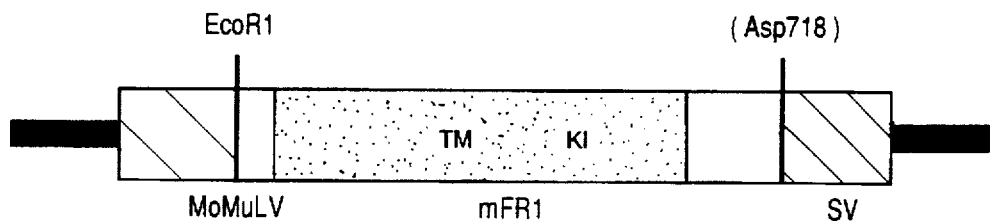
FIG. 2 is a schematic diagram of the mouse FGF receptor expression vector Mo/mFR/SV, in which "TM" represents the transmembrane domain; "KI" represents the tyrosine kinase domain; "SV" represents the SV40 splice and polyadenylation sequences; the stippled region represents the coding sequence and the solid bar represents the bluescript SK vector.

To express mFR in tissue culture, the plasmid Mo/mFR/SV was constructed. Using standard methods, a 3.2 kb EcoR1-Asp 718 restriction fragment from mFR was cloned downstream from the 675 bp MoMuLVLTR (Shinnick et al., Nature 293:543–548, 1981) and upstream of the SV40 splice and polyadenylation sequences (Seed, Nature 329:840–842, 1987) in the bluescript-SK vector (Stratagene), as shown in FIG. 2. This sequence contains 282 bp of the 5' untranslated sequence and 453 bp 3' of the mFR termination codon.

Cell lines and Transfection

The following cell lines were used: Balb/c fibroblasts; NIH 3T3 cells; CHO K1 cells (parental wild-type CHO cells, available as ATCC Accession No. CCL 61); clones 803 and 677, each of which is a clone of glucuronosyltransferase-deficient CHO K1 cells which lack cell-surface HSPG (in addition, 677 cells overexpress the closely related GAG, chondroitin sulfate); and clone 606, HS-N-sulfotransferase-deficient CHO K1-derived cells which express normal levels of (but undersulfated) cell surface HSPG. The mutant clones 803, 677, and 606 were obtained from Dr. Jeffrey D. Esko. Wild-type and mutant CHO cells were routinely grown in Hams F12 medium supplemented with 10% bovine fetal calf serum and L-glutamine (Sigma). For transfection of the murine FGF receptor, approximately $4 \times 10^7$ cells were trypsinized, washed in ice cold PBS, and incubated with 50 µg Mo/mFR/SV and 8 µg of CMV B-gal (source; used as a control for transfection efficiency) for 10 min at 4° C. Electroporation was done in a Bio-Rad Gene Pulser at 960 uF and 300V. Cells were then plated in 3 cm, 6-well plates, medium was replaced after 24 hours, and b-gal and binding assays were performed 36 to 48 hours after electroporation. Routinely, 30 to 40% of the cells stained positive for b-gal.

Radiolabeling of Recombinant Human bFGF

Recombinant human bFGF was labeled with $^{125}I$ (17 Ci/mg) (New England Nuclear, Boston, MA) using Iodo-beads (Pierce Chemical Co., Rockford, IL) according to the manufacturer's instructions. Full biological activity of bFGF was retained after iodination, as determined by its ability to stimulate serum-starved Balb/c fibroblasts. When subjected to SDS-PAGE, $^{125}I$-bFGF migrated as a single band in the same position as unlabeled bFGF.

Receptor Binding and Crosslinking of $^{125}I$-bFGF

Subconfluent cultures of about $2 \times 10^5$ cells in a 30 mm dish (Costar) were precooled to 4° C., washed twice with cold Dulbecco's modified Eagle's medium supplemented with 25 mM HEPES pH 7.5 and 1% bovine serum albumin (DMEM/BSA), and incubated for 2 hours at 4° C. with $^{125}I$-bFGF (50 µCi/ mmole) in DMEM/BSA at different concentrations and in the presence or absence of heparin, as determined by the experimental protocol. The binding medium was then discarded and the cells washed twice with ice cold PBS and twice with DMEM/BSA. To determine the amount of low-affinity-bound bFGF, the cells were incubated twice for 5 minutes with cold PBS, pH 7.5, containing 1.6M NaCl (low-affinity-bound bFGF could be totally removed using salt concentrations of 0.8M and higher--data not shown), and the radioactivity of the salt extraction solution assayed in a gamma counter. High-affinity-bound bFGF was determined by a 2M NaCl (pH 4.0) extraction (Moscatelli, J. Cell Biol. 107:753–759, 1988). Nonspecific binding was determined by including a 100-fold excess of unlabeled bFGF. After binding in the presence or absence of heparin, bFGF-receptor crosslinking with disuccinimidyl suberate (DSS) was performed as described (Yayon and Klagsbrun, Proc. Natl. Acad. Sci. USA 87:5346–5350, 1990). Briefly, cells were washed twice with PBS and then incubated with 0.15 mM DSS in PBS for 15 minutes at room temperature. The cells were then washed with a solution of 50 mM Tris, pH 7.4, and 100 mM glycine; and scraped and lysed in a small volume of lysis buffer containing 150 mM NaCl, 20 mM Tris pH 8.0, 1mM $MgCl_2$, 0.1 mM $ZnCl_2$, 0.5% NP-40 (Sigma), 1 µg aprotinin (Sigma), 1 µg/ml leupeptin (Sigma), and 2 mM PMSF (phenylmethylsulfonyl fluoride; Sigma). The cell lysate, cleared by spinning down nuclei and cell debris, was boiled and then electrophoresed under reducing conditions on a 7% SDS polyacrylamide gel. After drying the gel, an autoradiogram was prepared using Kodak X-Omat AR film (Eastman Kodak Co., Rochester, N.Y.).

Figure 1A:
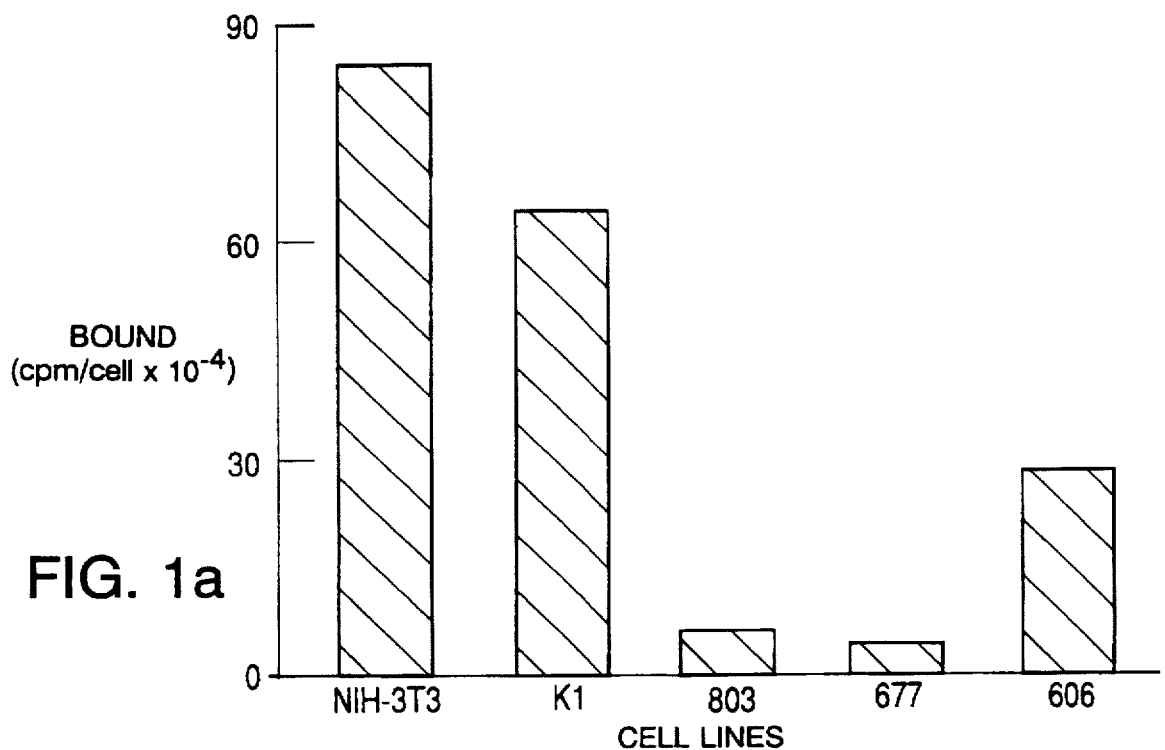
FIG. 1 is a pair of bar graphs illustrating (A) low affinity and (B) high affinity binding of $^{125}$I-bFGF to wild-type NIH-3T3 cells, wild-type CHO K1 cells, cells from clones 803 and 677 (lacking cell-surface HSPG), and cells from clone 606 (having undersulfated cell-surface HSPG).

Results
Basic FGF Binds Specifically to Cell Surface Heparan Sulfate Proteoglycans CHO cell mutants defective at different stages of glycosaminoglycan metabolism (Esko et al., Science 241:1092–1096, 1988), and which also naturally express very low levels of high-affinity FGF receptors (Mansukhani et al., Proc. Natl. Acad. Sci. USA 87:4378–4382, 1990), were used as a model system for analyzing the low-affinity binding sites for bFGF (FIG. 1A). Wild-type CHO cells (K1 cells) were capable of binding bFGF to low-affinity sites in a manner comparable to that found for NIH-3T3 cells. Clone 803 cells (defective in metabolism of heparin sulfate due to glucoronosyl-transferase deficiency and which possess about 5%–10% of the HSPG found in wild-type CHO K1 cells: Esko et al., Science 241:1092–1096, 1988) did not bind significant amounts of bFGF. Absence of low-affinity bFGF binding was similarly observed in experiments using clone 677, which bears the same enzymatic defect and has undetectable levels of HSPG, but which overexpresses the closely related GAG chondroitin sulfate. Compared to wild-type CHO cells, low-affinity binding of bFGF was reduced by more than 50% in CHO clone 606, a mutant expressing undersulfated HSPG (Bame and Esko, J. Biol. Chem. 264:8059–8065, 1989), confirming a previous report suggesting that the degree of sulfation of heparin can significantly alter its ability to bind aFGF (Sudhalter et al., J. Biol. Chem. 264:6892–6897, 1989). Taken together, these results directly demonstrate that the low-affinity binding sites for bFGF are cell surface and extracellular matrix HSPG.

Cloning the Murine FGF Receptor

Figure 1B:
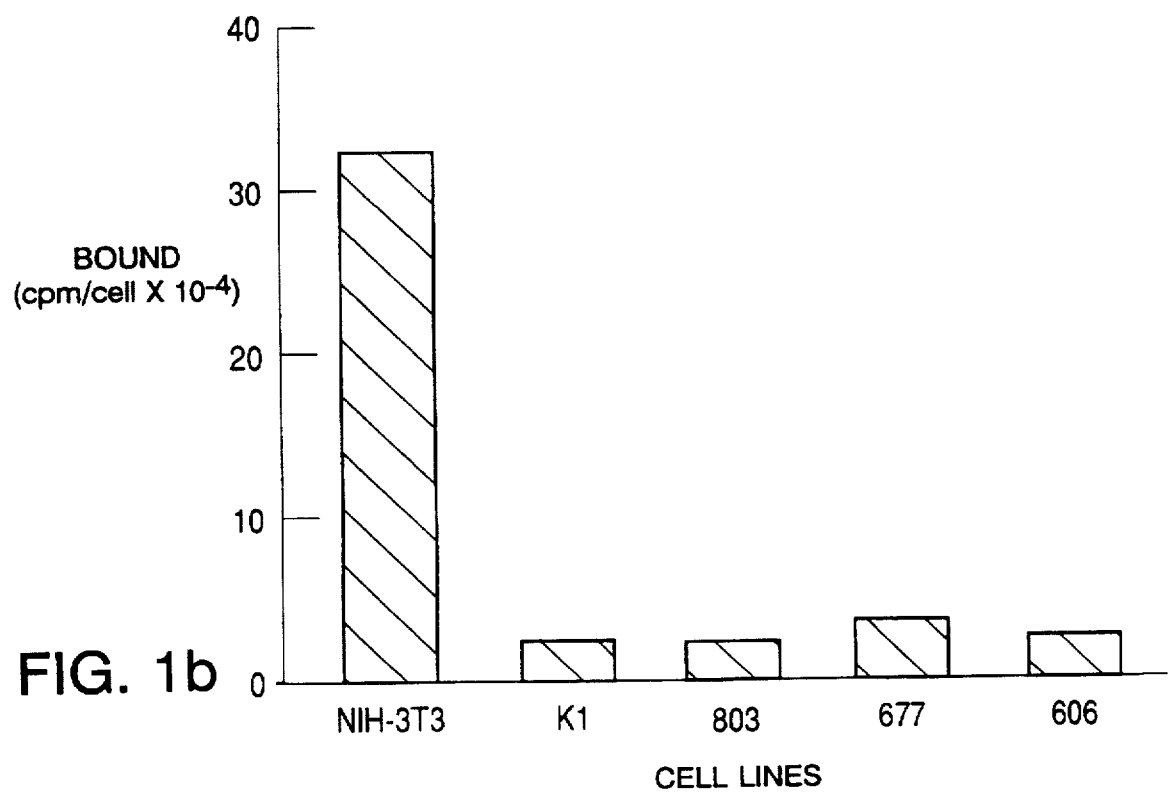

In agreement with a previous report (Mansukhani et al., 1990), wild-type as well as the mutant CHO cells tested express very low levels of high-affinity FGF receptors and exhibited very little high-affinity binding of bFGF when compared to NIH-3T3 cells (FIG. 1B). To investigate the binding properties of the FGF receptor in these HSPG-deficient cells, we cloned a murine homologue of the chicken and human FGF receptors, and constructed a vector to express it efficiently in cultured cells. The strategy used to clone the murine FGF receptor utilized a sequence comparison between chicken (CEK1) and human (hflg) FGF receptor cDNAs and mouse tyrosine kinase cDNA, MBEK. PCR primers designed to match regions highly conserved among these known sequences were used to amplify murine liver cDNA. Comparison of the amplified murine cDNA to CEK1, hPLG, and mBEK revealed that it was more similar to the CEK and flg sequence than to the mBEK sequence (84%, 90%, and 74%, respectively). This amplified murine cDNA, which we have named mFR, was then used to screen a murine brain cDNA library. Of twelve clones analyzed, one contained a 3.5 kb insert, which when sequenced was found to be highly homologous to both CEK1 and hflg and identical to the recently published murine flg (Reid et al., Proc. Natl. Acad. Sci. USA 87:1596–1600, 1990; Safran et al., Oncogene 5:635–643, 1990).

To express mFR in cultured cells, a 3.2 kb fragment containing the entire coding sequence of mFR was cloned downstream of the Molony murine leukemia virus long terminal repeat (MoMuLVLTR), and provided with heterologous splice and polyadenylation sequences derived from SV40 (FIG. 2). This plasmid, Mo/mFR/SV, was transfected into the wild type CHO cell line K1. Binding of $^{125}$I-bFGF was measured after transient transfection of CHO cells with mFR. The transiently-transfected wild-type CHO cells bound 8–10 fold more $^{125}$I-bFGF than did untransfected cells (FIG. 3A), indicating that the Mo/mFR/SV plasmid was efficiently expressed and translated to yield a functional FGF receptor.

Figure 3A:
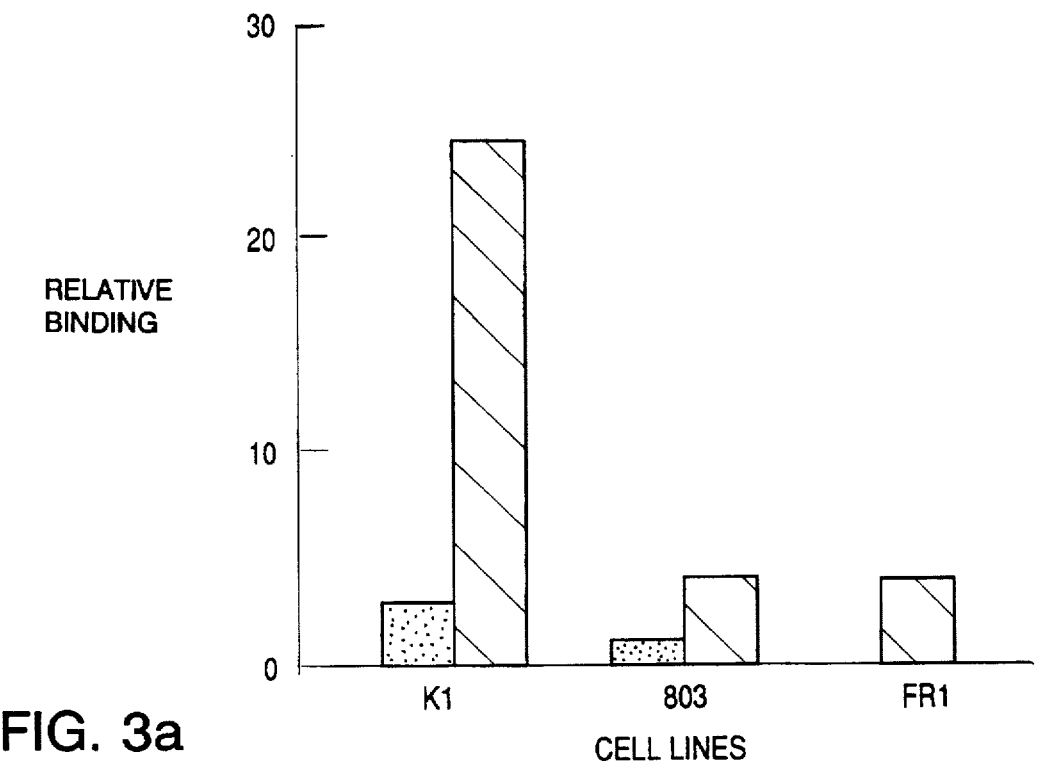
FIG. 3 is a pair of bar graphs illustrating relative degrees of high-affinity receptor binding by $^{125}$I-bFGF in the absence (A) or in the presence (B) of 40 ng/ml heparin, determined before (stippled bars) or 48 hours after (solid bars) transient transfection of mFR into CHO K1 and 803 cells; also shown is the relative binding of 803-FR1 cells, a clone of 803 cells stably transfected with mFR.
Figure 3B:
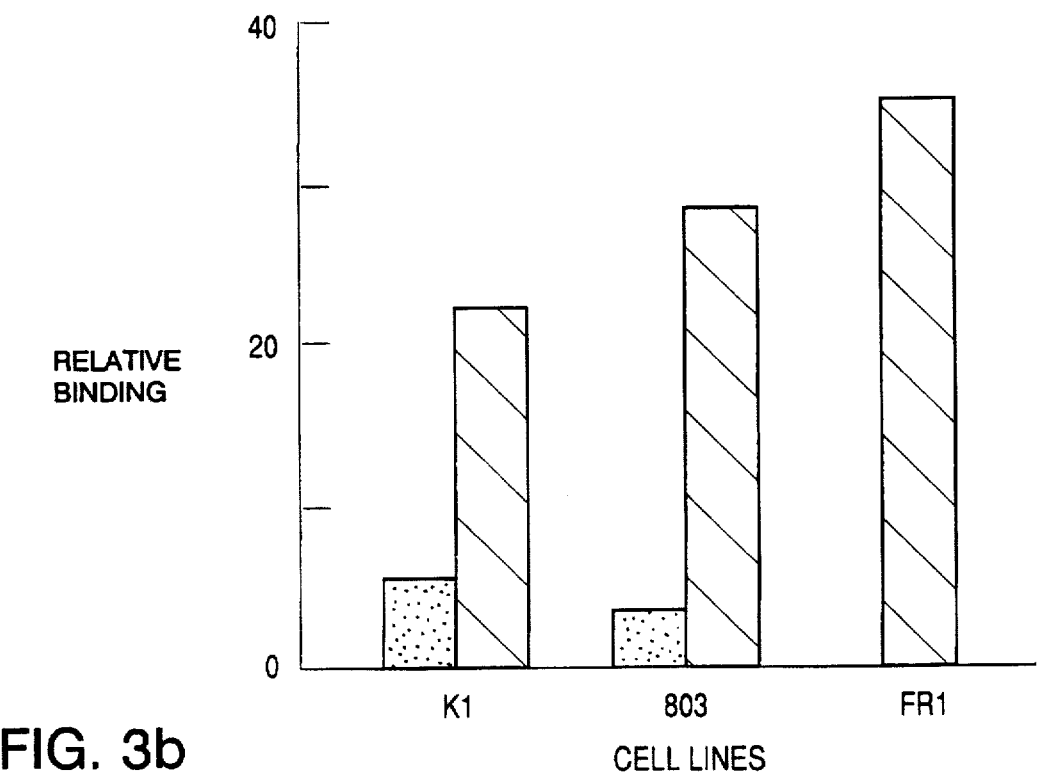

CHO Mutants Transfected with High-affinity FGF-receptor as a Model for Studying High- and Low-affinity Receptor Interactions Wild type CHO K1 cells transfected with the Mo/mFR/SV plasmid demonstrated high levels of high-affinity binding of bFGF (FIG. 3A). However, none of the similarly transfected HS-deficient mutants showed significant high-affinity binding of bFGF. High-affinity receptor binding of bFGF in these mFR1-transfected, HS-deficient mutants could be fully restored by inclusion of heparin in the binding medium (FIG. 3B). Heparin-dependent receptor binding was demonstrated independently in two HS-deficient, transiently transfected clones (clones 803 and 677) and in an isolated, stably expressing, HS-deficient clone (clone 803-FR1). These results suggest that cell surface low-affinity-binding HSPGs are needed to promote high-affinity bFGF binding, but that soluble heparin can substitute.

Figure 4:
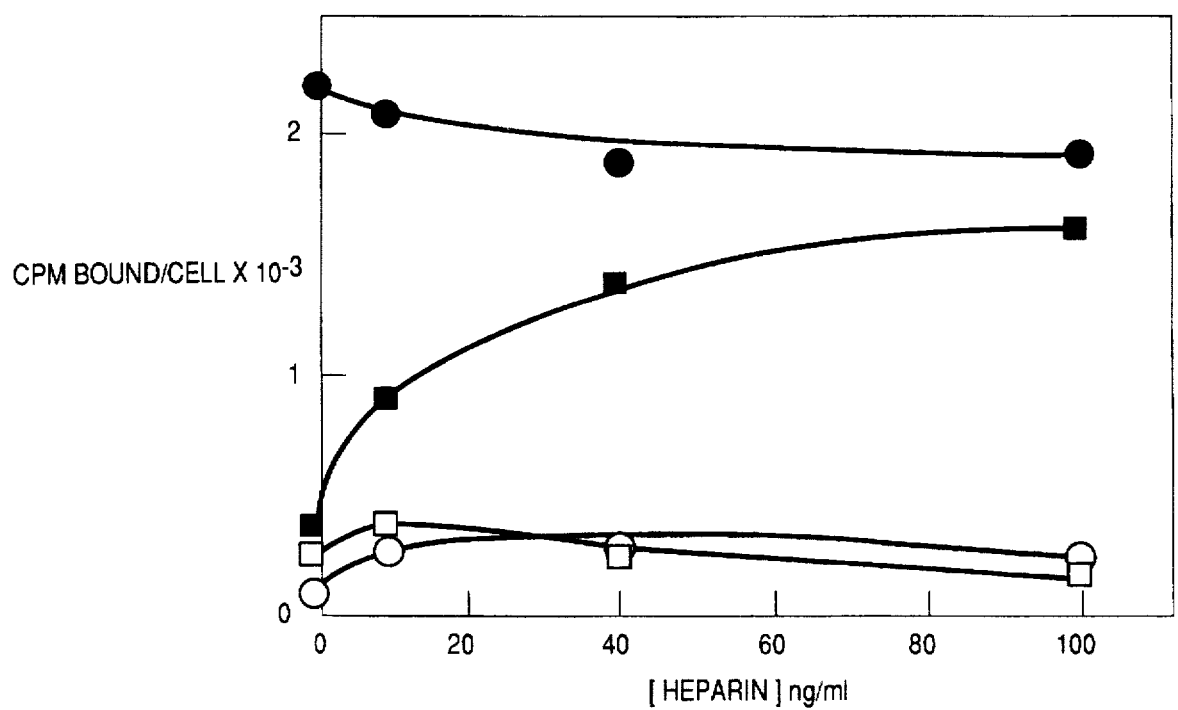
FIG. 4 is a graph illustrating the effect of heparin concentration on bFGF binding in CHO K1 cells (circles) and 803 cells (squares), expressing (closed symbols) and not expressing (open symbols) mFR.

Shown in FIG. 4A is a dose-response curve illustrating the effect of varying concentrations of heparin on binding of bFGF to its high-affinity receptor. These results demonstrate a saturable binding curve with maximal receptor binding at heparin concentrations as low as 40 ng/ml, suggesting a highly specific bFGF-heparin interaction. As expected, there was no detectable potentiating effect of heparin on the high-affinity binding of bFGF mFR-transfected wild type CHO K1 cells, which express ample cell surface HSPG. These cells register high levels of bFGF binding both in the presence and in the absence of heparin, suggesting that exogenously-applied heparin and cell surface HS or heparin-like molecules can interchangeably function as accessory molecules to promote binding of bFGF to the high-affinity FGF receptor.

Figure 5A:
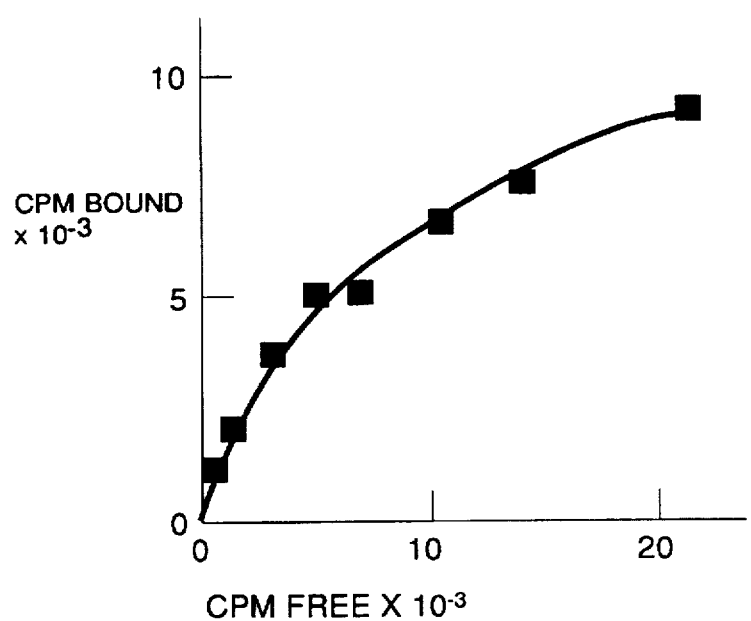
FIG. 5 is a triad of graphs illustrating high-affinity receptor binding of $^{125}$I-bFGF to HS-deficient cells expressing FGF receptors: (A) bound bFGF as a function of concentration of free bFGF in the presence of 40 ng/ml heparin; (B) binding in the presence (+) or absence (−) of excess unlabelled bFGF; and (C) time course for high-affinity binding to HS-deficient, FGF receptor-expressing cells, with 1 µg/ml heparin added at time zero.
Figure 5B:
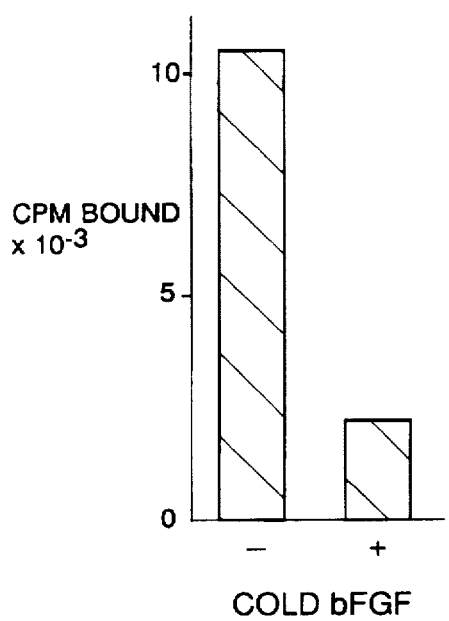
Figure 5C:
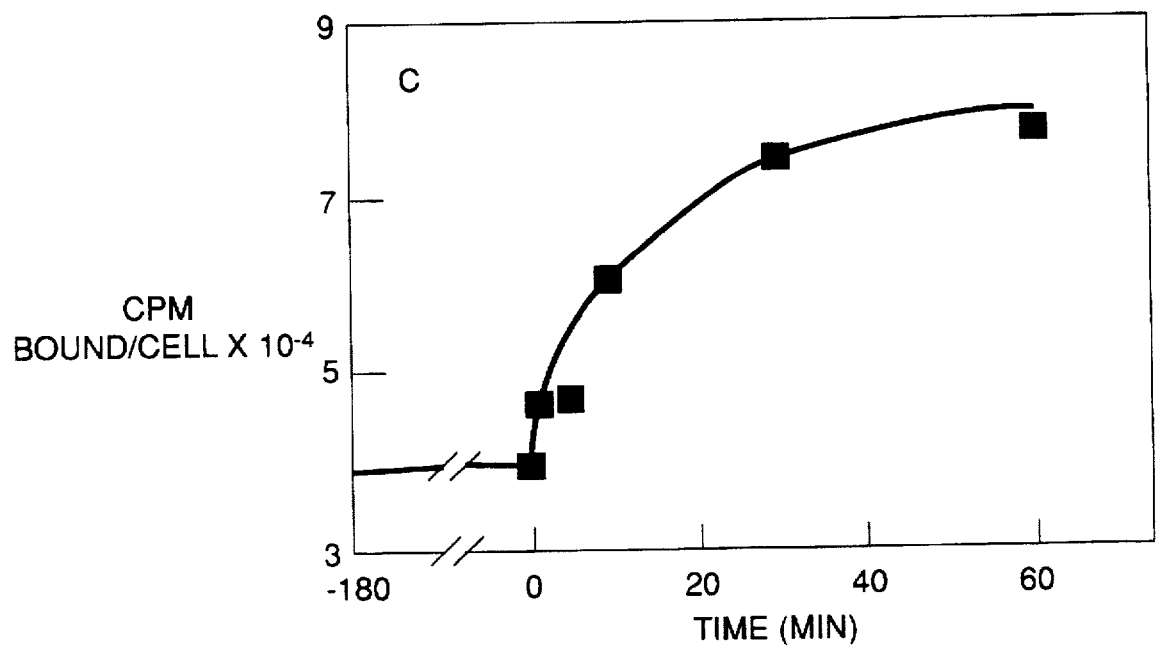

Basic FGF-receptor binding to HS-deficient cells in the presence of 40 ng/ml heparin revealed a specific, saturable, single class of high-affinity binding sites (FIG. 5A). The heparin-dependent high-affinity receptor binding was similar to that reported for non-heparin-dependent binding of bFGF to cells which naturally express both HSPG and high-affinity receptors for bFGF (Neufeld et al., J. Biol. Chem. 261:5631–5637, 1985). Similarly, heparin-dependent, high-affinity receptor binding was specifically competed out by an excess of unlabeled bFGF (FIG. 5B). A kinetic study of the effect of heparin on high-affinity bFGF binding to HS-deficient cells revealed a very rapid response to exogenously-added heparin, with a half-maximal response time at 4° C. of less than 10 minutes (FIG. 5C). Such a rapid response strongly suggests that binding of bFGF to heparin or cell surface HSPG is a rate-limiting step in the binding of bFGF to its high-affinity receptor. In addition, this result implies that the ability to restore high-affinity receptor binding by heparin is not due merely to stabilization of bFGF by heparin (Gospodarowicz and Chen, J. Cell Physiol 128:475–484, 1986; Saskela et al., J. Cell. Biol. 107:743–751, 1988), as high-affinity bFGF binding could be rapidly and fully restored even after a 3 hour preincubation in the absence of heparin. Moreover, aliquots of the binding medium, taken at the end of each experiment with or without heparin, showed no signs of degradation of bFGF, as evidenced by gel electrophoresis and a biological activity assay (not shown). Taken together, these results suggest that the ability of heparin to promote high-affinity receptor binding is not due to its stabilizing effect, but rather to its ability to confer upon bFGF an active, receptor-compatible conformation.

The Ability to Reconstitute High-affinity Binding is Specific to Heparin

Figure 6:
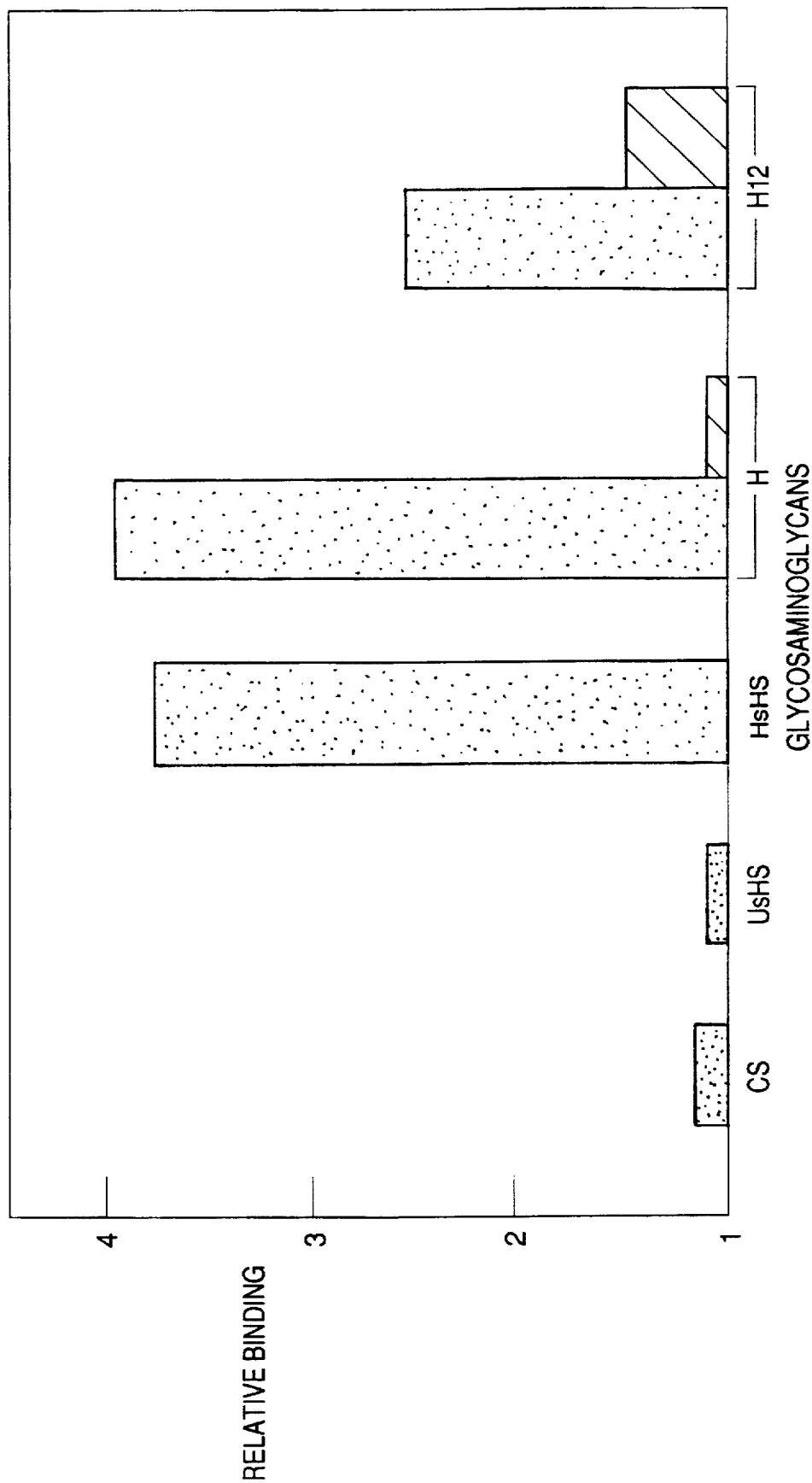
FIG. 6 is a pair of bar graphs illustrating relative $^{125}$I-bFGF binding to 803-FR1 cells in the absence or presence of chondroitin sulfate ("CS"); under-sulfated, kidney-derived HS ("UsHS"); highly-sulfated lung-derived HS ("HsHS"); heparin ("H"); or a 12-sugar heparin fragment ("H12"); or after incubation of heparin or the heparin fragment with heparinase prior to the binding assay (hatched bars).

The specificity of heparin in promoting high-affinity receptor binding was demonstrated by comparing the effect of heparin to that of each of the following: the closely related glycosaminoglycan chondroitin sulfate; an undersulfated kidney-derived HS; a highly-sulfated lung-derived HS; and a small, chemically-defined, twelve-sugar heparin fragment. While both chondroitin sulfate and the undersulfated HS did not promote high-affinity receptor binding, the sulfated HS was as active as heparin and the twelve-sugar heparin fragment was 70% as active as full-length heparin (FIG. 6A). Moreover, pretreatment of active heparin preparations with heparinase, a specific heparin-degrading enzyme, completely abolished their capacity to restore high-affinity receptor binding (FIG. 6B), suggesting that heparin is indeed the active fraction in these preparations.

Chemical Crosslinking of $^{125}$I-bFGF to Wild-type and HS-deficient CHO Cells

Figure 7:
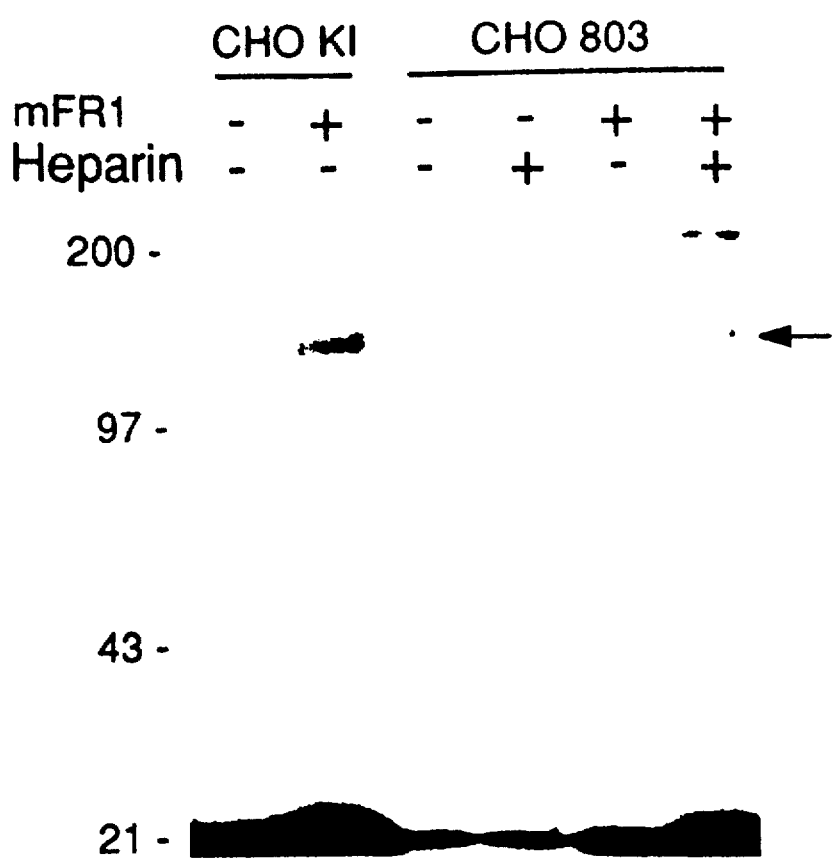
FIG. 7 is a copy of an autoradiogram illustrating the size, as assayed by PAGE, of the species labelled by crosslinking $^{125}$I-bFGF to wild-type (CHO K1) and mutant (CHO 803) cells transiently transfected with Mo/MFR/SV, in the presence (+) or absence (−) of 40 ng/ml heparin.
Figure 8:
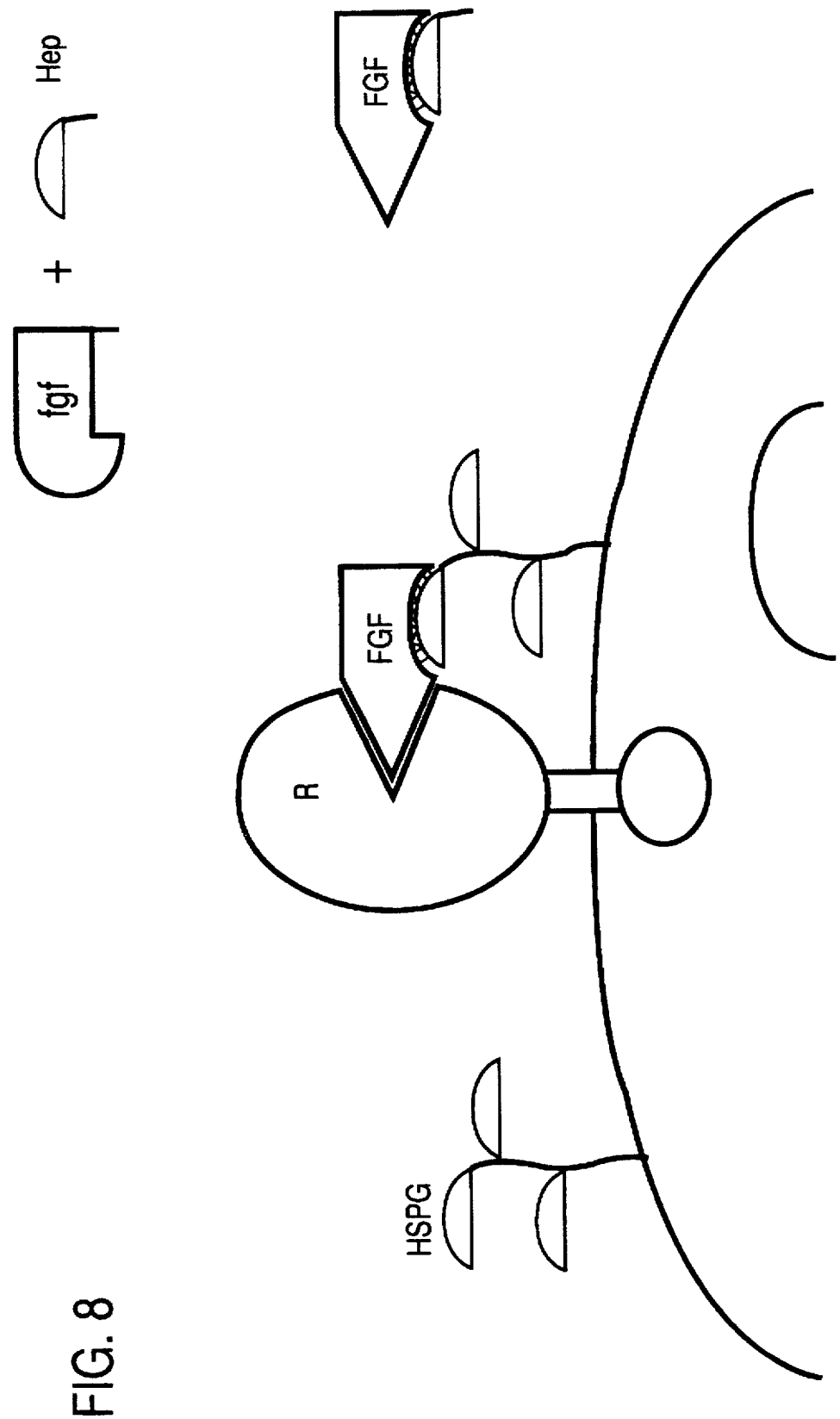
FIG. 8 is a schematic diagram illustrating a proposed "induced fit" model for heparin-dependent high-affinity-receptor binding of FGF, wherein heparin or cell-surface HSPG induces a conformational change in the FGF molecule, enabling it to bind to the high-affinity receptor (R).

Crosslinking of $^{125}$I-bFGF to wild-type CHO cells transfected with the mouse FGF receptor cDNA demonstrated a bFGF-receptor protein complex with an apparent molecular weight of 150 kD (FIG. 7), identical in size to that observed when $^{125}$I-bFGF is crosslinked to receptors on NIH-3T3 fibroblasts, which naturally express the FGF receptor (Yayon and Klagsbrun, Proc. Natl. Acad. Sci. USA 87:5346–5350, 1990). In contrast, bFGF could not be crosslinked to high-affinity receptors expressed on HS-deficient cells unless heparin was included in the binding medium prior to crosslinking. These results are in agreement with the radioreceptor binding data shown in FIG. 3, and provide further evidence for the failure of bFGF to bind to high-affinity receptors expressed in HS-deficient cells, confirming our observation that heparin or a heparin-like molecule is an absolute requirement for high-affinity receptor binding of bFGF.

EXAMPLE 2

Cell-Free System

Experimental Procedures
Recombinant Fusion Gene Construction

The mouse bFGF receptor/alkaline phosphatase fusion gene ("FRAP") was constructed by inserting a DNA sequence encoding a portion of the mouse bFGF receptor gene product into plasmid APtag-1, which encodes a secreted form of placental alkaline phosphatase (SEAP). The APtag-1 vector was constructed as described in Leder et al., USSN 07/593,764, herein incorporated by reference.

In APtag-1, the first codon of the mature SEAP protein (Berger et al., Proc. Natl. Acad. Sci. USA 84:4885, 1987, hereby incorporated by reference; Berger et al., Gene 66:1, 1988, hereby incorporated by reference) is immediately preceded by the nucleotide sequence: (SEQ ID NO.:2)

KpnI HindIII SnaBI BglII BspMII GG TAC CAA
GCT TAC GTA AGA TCT TCC GGA

This sequence includes cloning sites into which genes or gene fragments may be inserted to produce an APtag fusion protein. The structure of APtag-1 allows for the production of a fusion protein with an enzyme tag at its C-terminal end. The KpnI site shown above marks the 3' end of a 625 bp ClaI to KpnI fragment of the Moloney murine leukemia virus LTR; this fragment is flanked on its 5' side by sites for SnaBI, EcoRI, SalI and ClaI. The remainder of APtag-1 is the same as nucleotides 62 to 5212 of pBC12/PL/SEAP. Thus the relevant portion of APtag-1 includes, in the following order: restriction enzyme sites SnaBI, EcoRI, SalI, and ClaI; a 625 bp ClaI-KpnI fragment of the Moloney mouse leukemia virus LTR (Genebank Accession Nos. J02255, J02256, JP2257); the restriction enzyme sites KpnI, HindIII, SnaBI, BglII, and BspMII; and nucleotides 62 to 5212 of plasmid pBC12/PLAP (Berger et al., Gene 66:1, 1988), including a sequence encoding amino acids 1 to 489 of secreted placental alkaline phosphatase, a 3'-intronic region and the polyadenylation site of the rat preproinsulin II gene (Lomedico et al., Cell 18:545, 1979, hereby incorporated by reference), the SV40 origin of replication, and the entire sequence of pXF3, a poison sequence-minus derivative of pBR322 (Hanahan et al., J. Mol. Biol. 166:557, 1983, hereby incorporated by reference; Cullen et al., Cell 46:973, 1986, hereby incorporated by reference). The Ig heavy chain promoter and enhancer, the CMV enhancer, or the Rous sarcoma virus LTR may, for example, be used in place of the Moloney murine leukemia virus LTR to direct expression of the hybrid protein; and an SV40 intron and splice site may, for example, be used in place of the rat preproinsulin sequence.

SEAP was chosen as the enzyme tag for a number of reasons, including the availability of a variety of indicator substrates for alkaline phosphatases, the high specific activity of the mammalian enzymes, the high stability, including stability to heat, of the placental isozyme, and the availability of isozyme-specific inhibitors that can be used to reduce background phosphatase activities (Berger et al., Gene 66:1, 1988; Harlow and Lane, Antibodies:a laboratory manual, Cold Spring Harbor Laboratory, Cold Spring Harbor, N.Y., 1988, hereby incorporated by reference; Zoellner and Hunter, J. Histochem. Cytochem. 37:1893, 1989, hereby incorporated by reference). In addition, proteolytic digestion studies have indicated that both the N- and C-termini of the protein are dispensable for activity (Jemmerson et al. in Human Alkaline Phosphatases, T. Stigbrand & W. H. Fishman, Liss, N.Y., 1983, hereby incorporated by reference), making it likely that protein fusions at either end would leave the enzyme activity intact.

Figure 11:
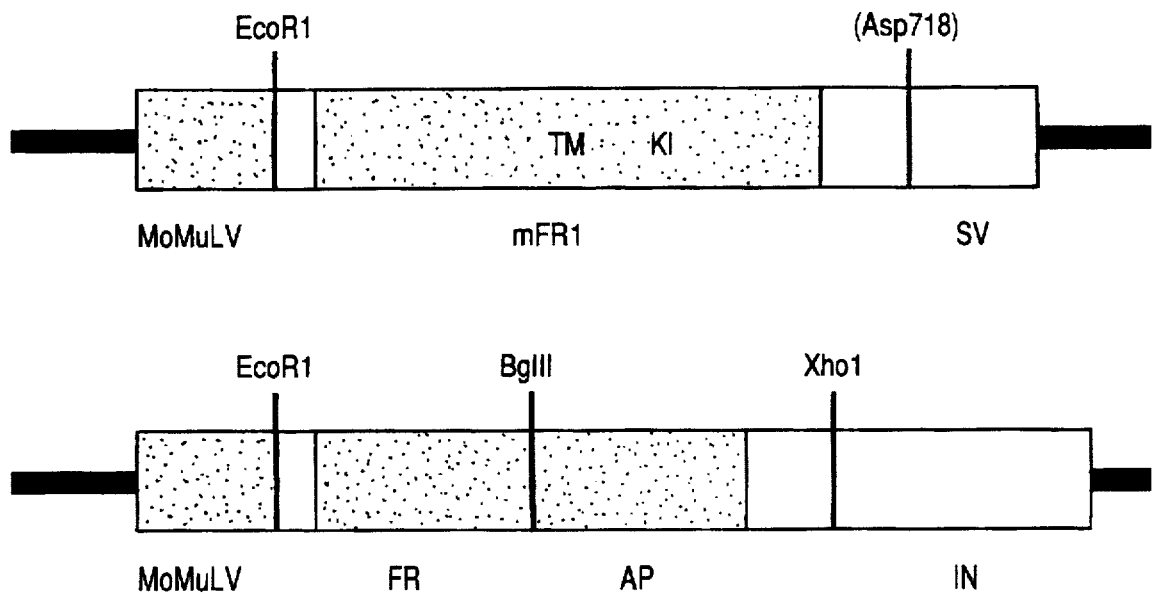
FIG. 11 is a pair of schematic diagrams of the mFR1 plasmid and the FRAP plasmid.

To generate a FGF receptor/SEAP fusion protein, the 5' end of a mouse bFGF receptor cDNA sequence, including sequences encoding the FGF secretion signal peptide and the entire extracellular domain (i.e., ending at amino acid 374, immediately before the first hydrophobic amino acid of the transmembrane region), was inserted into APtag-1. The Mo/mFR/SV plasmid described in the related Yayon et al. patent application was cut with ClaI and HincII to produce a DNA fragment containing the Molony virus LTR and most of the sequence of mFR 5' of the transmembrane domain, up to the HincII restriction site at nucleotide 1342. This fragment was incorporated into ClaI/BglII-digested APtag in a three-way ligation using as a linker a PCR fragment which includes a sequence encoding (a) the remainder of mFR adjacent to the transmembrane domain, and (b) a BglII restriction site. This PCR fragment was generated from the mFR template, using a 5' primer (GGAGATCTCCCATCACTCTGCATGGTTG) (SEQ ID NO.:3) which corresponds to nucleotides 1317–1343 of the mFR sequence (just 5' to the HincII site), and a 3' primer (CGGAAGATCTCTCCAGGTAGAGCG) (SEQ ID NO.:4) corresponding to nucleotides 1390–1404 of the mFR sequence plus (at its 5' end) a BglII restriction site. The three-way ligation resulted in a plasmid having the structure diagrammed in FIGS. 10 and 11. Sequencing confirmed the open reading frame at the two ligation points flanking the PCR fragment.

Expression of the FRAP Fusion Protein

The FRAP fusion protein was produced in a mammalian cell line stably transfected with the FRAP plasmid, as follows: the FRAP plasmid was linearized with ClaI and was co-transfected, along with the selectable marker plasmid CMVNeo (described in Schmidt et al., Mol. Cell Biol. 10:4406–4411, 1990, hereby incorporated by reference), into NIH 3T3 cells using the electroporation technique described in Potter et al., Proc. Natl. Acad. Sci. 81:7161, 1984, hereby incorporated by reference. Cells were then grown in DMEM (Sigma) containing 10% bovine calf serum (Hyclone Laboratories Inc., Logan, UT), and after selection with 400 μg/ml G418 (Life Technologies Inc., Grand Island, N.Y.), approximately 100 neo$^R$ clones were screened for secretion of placental alkaline phosphatase activity. The alkaline phosphatase assay was performed by heating a portion of the supernatant at 65° C. for 10 min to inactivate background phosphatase activity, and then measuring the $OD_{405}$ following incubation in a solution of 1M diethanolamine, pH 9.8 (Sigma); 0.5 mM $MgCl_2$; 10 mM L-homoarginine (a phosphatase inhibitor; Sigma) 0.5 mg/ml BSA (Sigma cat.no. A-7638); and 12 mM p-nitrophenyl phosphate (Sigma cat.no. 104–105), prepared as a single 2X stock solution. The highest AP-expressing clone, termed FRAP-A2, was used for production of the FRAP fusion protein. Further characterization of the FRAP-A2 fusion polypeptide is accomplished in accordance with the methods described in Leder et al., USSN 07/593,764.

Assay for FGF-binding Activity

Figure 12:
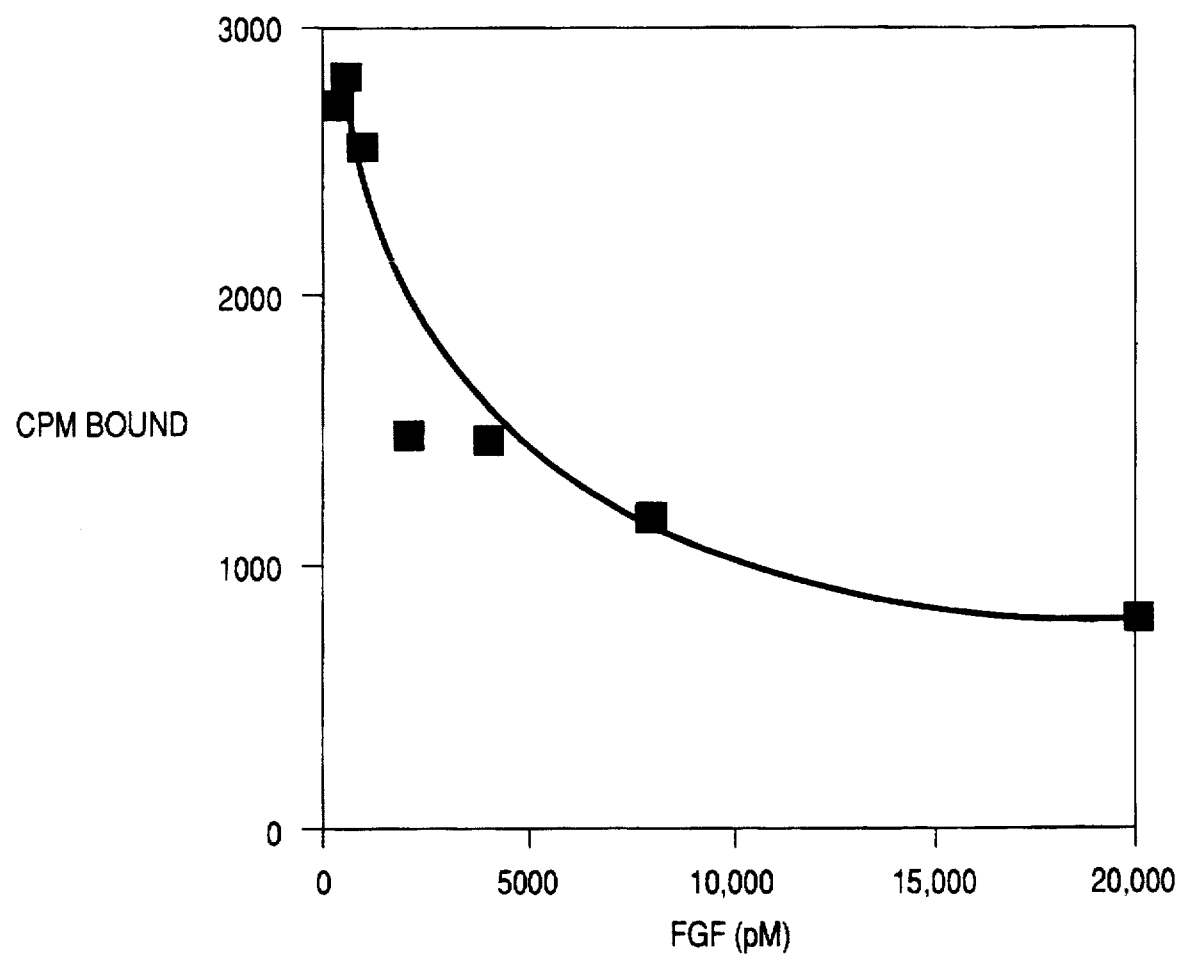
FIG. 12 is a graph illustrating a competition assay, wherein the amount of $^{125}$I-bFGF bound to FRAP in the presence of increasing amounts of unlabelled bFGF was measured.
Figure 13:
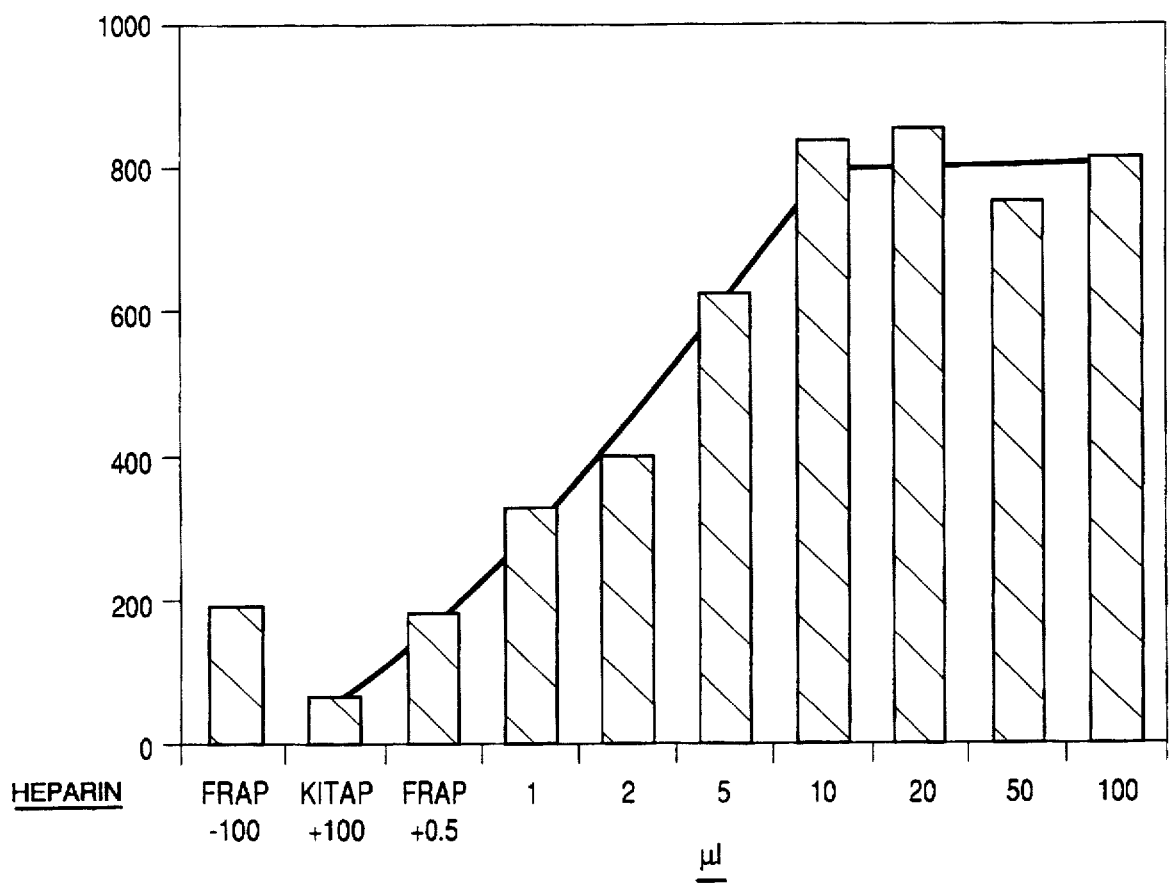
FIG. 13 is a bar graph illustrating that as the amount of FRAP protein present in the assay sample increases (indicated as ul of conditioned medium derived from cells transfected with and expressing the FRAP plasmid), the amount of $^{125}$I-bFGF bound to and immunoprecipitated by the AP-specific monoclonal antibody increases.
Figure 14:
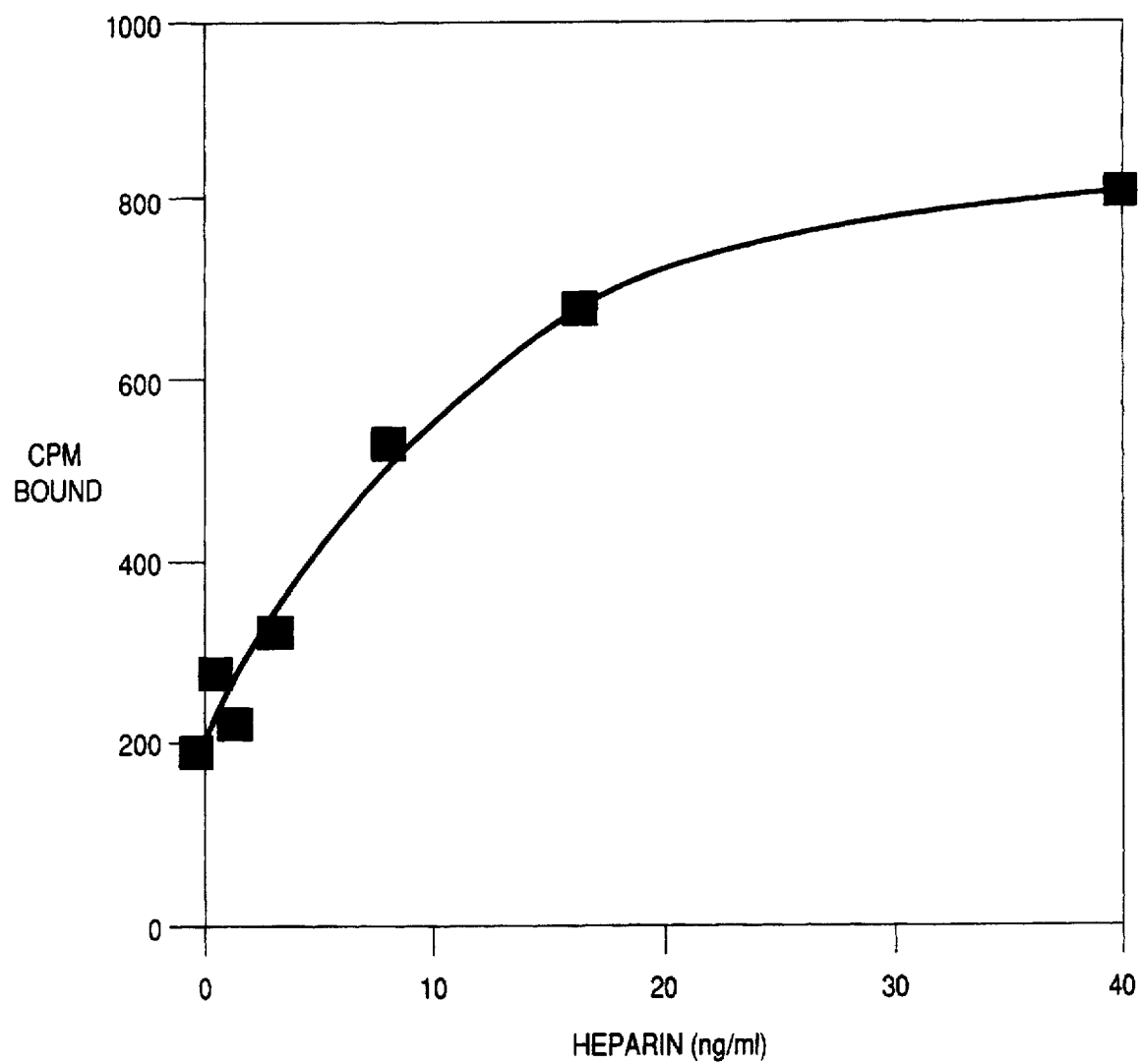
FIG. 14 is a graph showing the dependence on heparin concentration of binding of $^{125}$I-bFGF to FRAP protein (as immunoprecipitated by the AP-specific monoclonal antibody)

Conditioned medium from FRAP-A2 was assayed for its ability to bind $^{125}$I-bFGF by combining in the presence or in the absence of a standard amount of heparin, an aliquot of conditioned medium with a standard amount of $^{125}$I-bFGF and a standard amount of monoclonal antibody specific for placental alkaline phosphatase (Medix Biotech, Foster City, Calif.) coupled to CNBr-activated sepharose beads (Pharmacia, Piscataway, N.J.). The mixture was incubated for 90 min at 4° C. and centrifuged to pellet the beads, which were then washed two times with 0.5 ml PBS and re-pelleted before determining the amount of bound $^{125}$I in a gamma counter. FIG. 12 shows the results of a competition assay in which bound $^{125}$I was found to decrease with increasing concentrations of unlabelled FGF. In the experiment illustrated in FIG. 13, varying amounts of FRAP-A2-conditioned medium were combined with heparin and $^{125}$I-bFGF, while in FIG. 14 the variable was the concentration of heparin in the assay mix.

Other embodiments of the invention are within the following claims.

SEQUENCE LISTING ( 1 ) GENERAL INFORMATION:

( i i i ) NUMBER OF SEQUENCES: 6

( 2 ) INFORMATION FOR SEQ ID NO: 1:

( i ) SEQUENCE CHARACTERISTICS:
        ( A ) LENGTH: 3503
        ( B ) TYPE: nucleic acid
        ( C ) STRANDEDNESS: single
        ( D ) TOPOLOGY: linear ( x i ) SEQUENCE DESCRIPTION: SEQ ID NO: 1:

```
GGAATTCGGC  ACGAGCGCCC  GGGCTGGAGG  CGCCCGGCTC  GGAGTGCCGC  CGGGAGTCGT    60

GCCTCGGCCG  CGGAGCCCTC  GAGACCCCAT  CAGGATCTGA  ACGGAGCCCG  GAGACGAGCG   120

GCGGGACGCA  AGACACAGAC  ACCCSCCSCG  CCACGGACAG  CTCTCCAGAG  GCGGGACCGC   180

AGCGCCAAGT  GAGAGTCAGC  TTGCGAAGGC  AGACCACGCT  CACGGTGGAA  TATCCATGGA   240

GGTACGGAGC  CTTGTTACCA  ACCTCTAACC  GCAGAACTGG  GATGTGGGGC  TGGAAGTGCC   300

TCCTCTTCTG  GGCTGTGCTG  GTCACAGCCA  CTCTCTGCAC  TGCCAGGCCA  GCCCCAACCT   360

TGCCCGAACA  AGCTCAGCCC  TGGGGAGTCC  CTGTGGAAGT  GGAGTCTCTC  CTGGTCCACC   420

CTGGCGACCT  CCTACAGCTT  CGCTGTCGGC  TTCGCGATGA  TGTGCAGAGC  ATCAACTGGC   480

TKSGGGATGG  GGTGCAGCTG  GTGGAGAGCA  ACCGTACCCG  CATCACAGGG  GAGGAGGTGG   540

AGGTGCGGGA  CTCCATCCCC  GCTGACTCTG  GCCTCTACGC  TTGCGTGACC  AGCAGCCCT    600

CTGGCAGCGA  TACCACCTAC  TTCTCCGTCA  ATGTCTCAGA  TGCACTCCCA  TCCTCGGAAG   660

ATGATGACGA  TGACCATGAC  TCCTCCTCGG  AGGAGAAAGA  GACGGACAAC  ACCAAACCAA   720

ACCCTGTAGC  TCCCTACTGG  ACATCCCCAG  AGAAAATGGA  GAAGAAACTG  CATCGGGTGC   780

CCGCTGCCAA  GACGGTGAAG  TTCAAGTGCC  CGTCGAGTGG  GACACCCAAC  CCCACTCTGC   840

GCTGGTTGAA  AAATGGCAAA  GAGTTTAAGC  CTGACCACCG  AATTGGAGGC  TACAAGGTTC   900
```

-continued

```
GCTATGCCAC CTGGAGCATC ATAATGGATT CTGTGGTGCC TTCTGACAAG GGCAACTACA    960
CCTGCATCGT GGAGAATGAG TATGGGAGCA TCAACCACAC CTACCAGCTT GACGTCGTGG   1020
AACGATCTCC GCACCGACCC ATCCTTCAGG CAGGGCTGSC TGCCAACAAG ACAGTGGCCC   1080
TGGGCAGCAA TGTGGAGTTC ATGTGTAAGG TGTACAGCGA TCCSMAGCCT CACATTCAGT   1140
GGCTGAAGCA CATCGAGGTG AACGGGAGTA AGATCGGGCC AGACAACTTG CCGTATGTCC   1200
AGATCCTGAA GACTGCTGGA GTTAATACCA CCGACAAGGA AATGGAGGTG CTTCATCTAC   1260
GGAATGTCTC CTTTGAGGAT GCGGGGGAGT ATACGTGCTT GGCGGGTAAC TCTATCGGAC   1320
TCTCCCATCA CTCTGCATGG TTGACCGTTC TGGAAGCCCT GGAAGAGAGA CCAGCTGTGA   1380
TGACCTCACC GCTCTACCTG GAGATCATTA TCTACTGCAC CGGGGCCTTC CTGATCTCCT   1440
GCATGTTGGG CTCTGTCATC ATCTATAAGA TGAAGAGCGG CACCAAGAAG AGCGACTTCC   1500
ATAGCCAGAT GGCTGTGCAC AAGCTGGCCA AGAGCATCCC TCTGCGCAGA CAGGTAACAG   1560
TGTCAGCTGA CTCCAGTGCA TCCATGAACT CTGGGGTTCT CCTGGTTCGG CCCTCACGGC   1620
TCTCCTCCAG CGGGACCCCC ATGCTGGCTG GAGTCTCCGA ATATGAGCTC CTGAGGATC    1680
CCCGCTGGGA GCTGCCACGA GACAGACTGG TCTTAGGCAA ACAACTTGGC GAGGGCTGCT   1740
TCGGGCAGGT GGTGTTGGCT GAGGCCATCG GGCTGGATAA GGACAAACCC AACCGTGTGA   1800
CCAAAGTGGC CGTGAAGATG TTGAAGTCCG ACGCAACGGA GAAGGACCTG TCGGATCTGA   1860
TCTCGGAGAT GGAGATGATG AAAATGATTG GGAAGCACAA GAATATCATC AACCTTCTGG   1920
GAGCGTGCAC ACAGGATGGT CCTCTTTATG TCATTGTGGA GTACGCCTCC AAAGGCAATC   1980
TCCGGGAGTA TCTACAGGCC CGGAGGNCTC CTGGGCTGGA GTACTGCTAT AACCCCAGCC   2040
ACAACCCCGA GGAACAGCTG TCTTCCAAAG ATCTGGTATC CTGTGCCTAT GACGTGGCTC   2100
GGGGCATGGA GTATCTTGCC TCTAAGAAGT GTATACACCG AGACCTGGCT GCTAGGAACG   2160
TCCTGGTGAC CGAGGATAAC GTAATGAAGA TCGCAGACTT TGGCTTAGCT CGAGACATTC   2220
ATCATATCGA CTACTACAAG AAAACCACCA ACGGGCGGCT GCCTGTGAAG TGGATGGCCC   2280
CTGAGGCGTT GTTTGACCGG ATCTACACAC ACCAGAGCGA TGTGTGGTCT TTTGGAGTGC   2340
TCTTGTGGGA GATCTTCACT CTGGGTGGCT CCCCATACCC CGGTSTGCCT GTGGAGGAAC   2400
TTTTCAAGCT GCTGAAGGAG GGTCATCGAA TGGACAAGCC CAGTAACTGT ACCAATGAGC   2460
TGTACATGAT GATGCGCGAC TGCTGGCATG CAGTGCCCTC TCAGAGACCT ACGTTCAAGC   2520
AGTTGGTGGA AGACCTGGAC CGCATTGTGG CCTTGACCTC CAACCAGGAG TATCTGGACC   2580
TGTCCATACC GCTGGACCAG TACTCACCCA GCTTTCCCGA CACACGGAGC TCCACCTGCT   2640
CCTCAGGGGA GGACTCTGTC TTCTCTCATG AGCCGTTACC TGAGGAGCCC TGTCTGCCTC   2700
GACACCCCAC CCAGCTTGCC AACAGTGGAC TCAAACGGCG CTGACTACCA ACCCTGTCCC   2760
CAGTTTTCTC CCATTCCGTC GTCACCCGTG CCCCTCACCC ACAATCCCCT TGTTGGACAC   2820
ACTGCCTTTC TCCTCCTCCT TTTCGCGCTG GAAAGAGGCC AGTGCCTGAC TGAGGCCTTC   2880
CTGTGTTGTG GGCCTTCCCC CTCCATCACC CCCAAGACCC CTCTTCTCCC TCTTCTTAGC   2940
CTGCTGTGTG AGAGAGGAGC CAAGAGGCAG GTGCTTGCCG ACGGCCGCAT CCTCCTTCCC   3000
AGGTGTTGGA CCAAGACCCG ACCCGCTGCC TGGCACTGCT TGGAGGTGTG CAGAGCGGAA   3060
GCAAGTGGAG AATCCGGGGC ATTCCTGTTG ACCCATCAGC CCCTTCTGTT CTGGCGGCAG   3120
GGGCCTTGGG GCTCCTGGAA GCCGTGAGGT TTCTGTTTAG GCCTTACCGA AGGCAACCTC   3180
TGCTCCAGAT GGATGGTACC AGTAGCTTCT TAATTCCAAT ACTAATTTGC TTTGCTGACC   3240
AAATACCTGC CTGGTACCAG AAGACAGGGA GGCAGAGACT GGGAGCCGTG ATGTGCCCTT   3300
```

```
GGGCTGAGCC CTAGACTTGG GGCTCTGTAC ATAGCTATGA AGAAAAACAC AAAGTGTATA      3360

AATCTTGAGT ATATATTTAC ATGTCTTTTT AAAAGGGTC  GTTACTAGAG ATTTACCATG      3420

GGGGAGACGC CCAGGGTAGC ATCCGTTGCT ATATATTAAA AACAAACGAA CAGAAAAAAA      3480

AAAAAAAAAA ACTCGAGGGG GGG                                              3503
```

( 2 ) INFORMATION FOR SEQ ID NO: 2:

( i ) SEQUENCE CHARACTERISTICS:
        ( A ) LENGTH: 29
        ( B ) TYPE: nucleic acid
        ( C ) STRANDEDNESS: single
        ( D ) TOPOLOGY: linear ( x i ) SEQUENCE DESCRIPTION: SEQ ID NO: 2:

```
GGTACCAAGC TTACGTAAGA TCTTCCGGA                                        29
```

( 2 ) INFORMATION FOR SEQ ID NO: 3:

( i ) SEQUENCE CHARACTERISTICS:
        ( A ) LENGTH: 28
        ( B ) TYPE: nucleic acid
        ( C ) STRANDEDNESS: single
        ( D ) TOPOLOGY: linear ( x i ) SEQUENCE DESCRIPTION: SEQ ID NO: 3:

```
GGAGATCTCC CATCACTCTG CATGGTTG                                         28
```

( 2 ) INFORMATION FOR SEQ ID NO:4:

( i ) SEQUENCE CHARACTERISTICS:
        ( A ) LENGTH: 24
        ( B ) TYPE: nucleic acid
        ( C ) STRANDEDNESS: single
        ( D ) TOPOLOGY: linear ( x i ) SEQUENCE DESCRIPTION: SEQ ID NO: 4:

```
CGGAAGATCT CTCCAGGTAG AGCG                                             24
```

( 2 ) INFORMATION FOR SEQ ID NO: 5:

( i ) SEQUENCE CHARACTERISTICS:
        ( A ) LENGTH: 28
        ( B ) TYPE: nucleic acid
        ( C ) STRANDEDNESS: single
        ( D ) TOPOLOGY: linear ( x i ) SEQUENCE DESCRIPTION: SEQ ID NO: 5:

```
CCGAATTCAT CTTCATCATC TCCATCTC                                         28
```

( 2 ) INFORMATION FOR SEQ ID NO:6:

( i ) SEQUENCE CHARACTERISTICS:
        ( A ) LENGTH: 820
        ( B ) TYPE: amino acid
        ( C ) STRANDEDNESS: single
        ( D ) TOPOLOGY: linear ( x i ) SEQUENCE DESCRIPTION: SEQ ID NO: 6:

```
                                            Met  Trp  Gly  Trp  Lys
                                             1                    5

Cys  Leu  Leu  Phe  Trp  Ala  Val  Leu  Val  Thr  Ala  Thr  Leu  Cys  Thr  Ala
               10                      15                      20

Arg  Pro  Ala  Pro  Thr  Leu  Pro  Glu  Gln  Ala  Gln  Pro  Trp  Gly  Val  Pro
               25                      30                      35
```

-continued

```
Val Glu Val Glu Ser Leu Leu Val His Pro Gly Asp Leu Leu Gln Leu
     40                  45                  50
Arg Cys Arg Leu Arg Asp Asp Val Gln Ser Ile Asn Trp Xaa Xaa Asp
     55              60                  65
Gly Val Gln Leu Val Glu Ser Asn Arg Thr Arg Ile Thr Gly Glu Glu
70                   75                  80                  85
Val Glu Val Arg Asp Ser Ile Pro Ala Asp Ser Gly Leu Tyr Ala Cys
             90                  95                      100
Val Thr Ser Ser Pro Ser Gly Ser Asp Thr Thr Tyr Phe Ser Val Asn
             105             110                 115
Val Ser Asp Ala Leu Pro Ser Ser Glu Asp Asp Asp Asp His Asp
             120             125                 130
Ser Ser Ser Glu Glu Lys Glu Thr Asp Asn Thr Lys Pro Asn Pro Val
        135             140                 145
Ala Pro Tyr Trp Thr Ser Pro Glu Lys Met Glu Lys Lys Leu His Arg
150                     155                 160                 165
Val Pro Ala Ala Lys Thr Val Lys Phe Lys Cys Pro Ser Ser Gly Thr
                 170             175                 180
Pro Asn Pro Thr Leu Arg Trp Leu Lys Asn Gly Lys Glu Phe Lys Pro
             185             190                 195
Asp His Arg Ile Gly Gly Tyr Lys Val Arg Tyr Ala Thr Trp Ser Ile
         200             205                 210
Ile Met Asp Ser Val Val Pro Ser Asp Lys Gly Asn Tyr Thr Cys Ile
     215                 220                 225
Val Glu Asn Glu Tyr Gly Ser Ile Asn His Thr Tyr Gln Leu Asp Val
230                 235                 240                 245
Val Glu Arg Ser Pro His Arg Pro Ile Leu Gln Ala Gly Leu Xaa Ala
             250             255                 260
Asn Lys Thr Val Ala Leu Gly Ser Asn Val Glu Phe Met Cys Lys Val
             265             270                 275
Tyr Ser Asp Xaa Xaa Pro His Ile Gln Trp Leu Lys His Ile Glu Val
             280             285                 290
Asn Gly Ser Lys Ile Gly Pro Asp Asn Leu Pro Tyr Val Gln Ile Leu
     295             300                 305
Lys Thr Ala Gly Val Asn Thr Thr Asp Lys Glu Met Glu Val Leu His
310                 315                 320                 325
Leu Arg Asn Val Ser Phe Glu Asp Ala Gly Glu Tyr Thr Cys Leu Ala
             330                 335                 340
Gly Asn Ser Ile Gly Leu Ser His His Ser Ala Trp Leu Thr Val Leu
             345                 350                 355
Glu Ala Leu Glu Glu Arg Pro Ala Val Met Thr Ser Pro Leu Tyr Leu
     360                 365                 370
Glu Ile Ile Ile Tyr Cys Thr Gly Ala Phe Leu Ile Ser Cys Met Leu
     375                 380                 385
Gly Ser Val Ile Ile Tyr Lys Met Lys Ser Gly Thr Lys Lys Ser Asp
390                 395                 400                 405
Phe His Ser Gln Met Ala Val His Lys Leu Ala Lys Ser Ile Pro Leu
             410                 415                 420
Arg Arg Gln Val Thr Val Ser Ala Asp Ser Ser Ala Ser Met Asn Ser
             425                 430                 435
Gly Val Leu Leu Val Arg Pro Ser Arg Leu Ser Ser Ser Gly Thr Pro
             440                 445                 450
Met Leu Ala Gly Val Ser Glu Tyr Glu Leu Pro Glu Asp Pro Arg Trp
```

-continued

| | 455 | | | | | 460 | | | | 465 | | | |
|---|---|---|---|---|---|---|---|---|---|---|---|---|---|
| Glu 470 | Leu | Pro | Arg | Asp | Arg 475 | Leu | Val | Leu | Gly | Lys 480 | Gln | Leu | Gly | Glu | Gly 485 |
| Cys | Phe | Gly | Gln | Val 490 | Val | Leu | Ala | Glu | Ala 495 | Ile | Gly | Leu | Asp | Lys 500 | Asp |
| Lys | Pro | Asn | Arg 505 | Val | Thr | Lys | Val | Ala 510 | Val | Lys | Met | Leu | Lys 515 | Ser | Asp |
| Ala | Thr | Glu 520 | Lys | Asp | Leu | Ser | Asp 525 | Leu | Ile | Ser | Glu | Met 530 | Glu | Met | Met |
| Lys | Met 535 | Ile | Gly | Lys | His | Lys 540 | Asn | Ile | Ile | Asn | Leu 545 | Leu | Gly | Ala | Cys |
| Thr 550 | Gln | Asp | Gly | Pro | Leu 555 | Tyr | Val | Ile | Val | Glu 560 | Tyr | Ala | Ser | Lys | Gly 565 |
| Asn | Leu | Arg | Glu | Tyr 570 | Leu | Gln | Ala | Arg | Arg 575 | Xaa | Pro | Gly | Leu | Glu 580 | Tyr |
| Cys | Tyr | Asn | Pro 585 | Ser | His | Asn | Pro | Glu 590 | Glu | Gln | Leu | Ser | Ser 595 | Lys | Asp |
| Leu | Val | Ser 600 | Cys | Ala | Tyr | Asp | Val 605 | Ala | Arg | Gly | Met | Glu 610 | Tyr | Leu | Ala |
| Ser | Lys 615 | Lys | Cys | Ile | His | Arg 620 | Asp | Leu | Ala | Ala | Arg 625 | Asn | Val | Leu | Val |
| Thr 630 | Glu | Asp | Asn | Val | Met 635 | Lys | Ile | Ala | Asp | Phe 640 | Gly | Leu | Ala | Arg | Asp 645 |
| Ile | His | His | Ile | Asp 650 | Tyr | Tyr | Lys | Lys | Thr 655 | Thr | Asn | Gly | Arg | Leu 660 | Pro |
| Val | Lys | Trp | Met 665 | Ala | Pro | Glu | Ala | Leu 670 | Phe | Asp | Arg | Ile | Tyr 675 | Thr | His |
| Gln | Ser | Asp 680 | Val | Trp | Ser | Phe | Gly 685 | Val | Leu | Leu | Trp | Glu 690 | Ile | Phe | Thr |
| Leu | Gly 695 | Gly | Ser | Pro | Tyr | Pro 700 | Gly | Xaa | Pro | Val | Glu 705 | Glu | Leu | Phe | Lys |
| Leu 710 | Leu | Lys | Glu | Gly | His 715 | Arg | Met | Asp | Lys | Pro 720 | Ser | Asn | Cys | Thr | Asn 725 |
| Glu | Leu | Tyr | Met | Met 730 | Met | Arg | Asp | Cys | Trp 735 | His | Ala | Val | Pro | Ser 740 | Gln |
| Arg | Pro | Thr | Phe 745 | Lys | Gln | Leu | Val | Glu 750 | Asp | Leu | Asp | Arg | Ile 755 | Val | Ala |
| Leu | Thr | Ser 760 | Asn | Gln | Glu | Tyr | Leu 765 | Asp | Leu | Ser | Ile | Pro 770 | Leu | Asp | Gln |
| Tyr | Ser 775 | Pro | Ser | Phe | Pro | Asp 780 | Thr | Arg | Ser | Ser | Thr 785 | Cys | Ser | Ser | Gly |
| Glu 790 | Asp | Ser | Val | Phe | Ser 795 | His | Glu | Pro | Leu | Pro 800 | Glu | Glu | Pro | Cys | Leu 805 |
| Pro | Arg | His | Pro | Thr 810 | Gln | Leu | Ala | Asn | Ser 815 | Gly | Leu | Lys | Arg | Arg 820 |

We claim:

1. A method for assaying the ability of a substance to bind to a high-affinity heparin-binding growth factor (HBGF) receptor, which method comprises combining said substance with
 (a) heparin or a heparin-like molecule, and
 (b) a test cell of a homogenous population of animal cells having on average a number of cell surface low-affinity HBGF-binding sites per cell less than 20% of the number of such binding sites found on wild-type CHO-K1 cells (ATCC Accession No. CCL61), and on average at least two times the number of cell surface high-affinity HBGF receptors per cell found on said CHO-K1 cells, and measuring the amount of said substance that binds to high-affinity HBGF receptors on said test cell.

2. The method of claim 1, wherein said test cell comprises a recombinant nucleic acid encoding said high-affinity HBGF receptor.

3. The method of claim 2, wherein said recombinant nucleic acid comprises the nucleic acid sequence of mFR.

4. The method of claim 2, wherein said recombinant nucleic acid is incorporated into the genome of said test cell.

5. The method of claim 2, wherein said recombinant nucleic acid is contained within a vector, and said test cell is transiently transfected with said vector.

6. The method of claim 1, wherein said high-affinity HBGF receptor is selected from the group consisting of acidic fibroblast growth factor (FGF) receptor, basic FGF receptor, int2 receptor, Kaposi's sarcoma FGF receptor, FGF-5 receptor, FGF-6 receptor, keratinocyte FGF receptor, chicken FGF receptor, and flg FGF receptor.

7. The method of claim 6, wherein said high-affinity HBGF receptor is a high-affinity bFGF receptor.

8. The method of claim 1, wherein said animal cells are mammalian cells.

9. A method for assaying the ability of a substance to affect the interaction of a given HBGF with a high-affinity HBGF receptor, which method comprises combining (a) a first cell of a homogenous population of animal cells having on average a number of cell surface low-affinity HBGF-binding sites per cell less than 20% of the number of such binding sites found on wild-type CHO-K1 cells (ATCC Accession No. CCL61), and on average at least two times the number of cell surface high-affinity receptors for said given HBGF per cell found on said CHO-K1 cells, with (b) said given HBGF in the presence of said substance;

combining a second cell of said homogenous population of animal cells with said given HBGF in the absence of said substance; and comparing the amount of said given HBGF bound to said first cell with the amount of said given HBGF bound to said second cell.

10. The method of claim 9, wherein said first cell and second cell comprise a recombinant nucleic acid encoding said high-affinity HBGF receptor.

11. The method of claim 10, wherein said recombinant nucleic acid comprises the nucleic acid sequence of mFR.

12. The method of claim 10, wherein said recombinant nucleic acid is incorporated into the genome of said test cell.

13. The method of claim 10, wherein said recombinant nucleic acid is contained within a vector, and said first cell and second cell are transiently transfected with said vector.

14. The method of claim 9, wherein said high-affinity HBGF receptor is selected from the group consisting of acidic FGF receptor, basic FGF receptor, int2 receptor, Kaposi's sarcoma FGF receptor, FGF-5 receptor, FGF-6 receptor, keratinocyte FGF receptor, chicken FGF receptor, and flg FGF receptor.

15. The method of claim 14, wherein said high-affinity HBGF receptor is a high-affinity bFGF receptor.

16. The method of claim 9, wherein said animal cells are mammalian cells.

17. A system for assaying the ability of a substance to bind to a high-affinity HBGF receptor, which system is a cell-free system that comprises (a) a hybrid molecule comprising a HBGF-binding portion of a naturally-occurring high-affinity HBGF receptor polypeptide covalently linked to an antigenic moiety, and (b) an amount of heparin or a heparin-like molecule sufficient to induce binding of an HBGF to said hybrid molecule.

18. The system of claim 17, wherein said HBGF-binding portion comprises the extracellular domain of a high-affinity HBGF receptor.

19. The system of claim 17, wherein said high-affinity HBGF receptor is selected from the group consisting of acidic FGF receptor, basic FGF receptor, int2 receptor, Kaposi's sarcoma FGF receptor, FGF-5 receptor, FGF-6 receptor, keratinocyte FGF receptor, chicken FGF receptor, and flg FGF receptor.

20. The system of claim 17, wherein said antigenic moiety comprises alkaline phosphatase.

21. The system of claim 20, wherein said HBGF receptor is a high-affinity bFGF receptor.

22. A system for assaying the ability of a substance to affect the interaction between a given HBGF and a high-affinity HBGF receptor, which system is a cell-free system that comprises (i) a test sample and (ii) a control sample, wherein said test sample comprises said given HBGF and a hybrid molecule comprising a HBGF-binding portion of a naturally-occurring high-affinity HBGF receptor polypeptide covalently linked to an antigenic moiety, and said control sample comprises said given HBGF, a hybrid molecule comprising a HBGF-binding portion of a naturally-occurring high-affinity HBGF receptor polypeptide covalently linked to an antigenic moiety, and heparin.

23. The system of claim 20, wherein said HBGF-binding portion comprises the extracellular domain of a high-affinity HBGF receptor.

24. The system of claim 22, wherein said high-affinity HBGF receptor is selected from the group consisting of acidic FGF receptor, basic FGF receptor, int2 receptor, Kaposi's sarcoma FGF receptor, FGF-5 receptor, FGF-6 receptor, keratinocyte FGF receptor, chicken FGF receptor, and flg FGF receptor.

25. The system of claim 22, wherein said antigenic moiety comprises alkaline phosphatase.

26. The system of claim 25, wherein said HBGF receptor is a high-affinity bFGF receptor.

27. A method for assaying the ability of a substance in a sample to bind to a high-affinity HBGF receptor, which method comprises (a) contacting said sample in a cell-free environment with (i) a hybrid molecule comprising a HBGF-binding portion of a naturally-occurring high-affinity HBGF receptor polypeptide covalently linked to an antigenic moiety, and (ii) an amount of heparin or heparin-like molecule sufficient to induce binding of an HBGF to said hybrid molecule to form an affinity complex;

(b) removing unbound substance; and (c) detecting said affinity complex.

28. A method for assaying the ability of a substance to affect the interaction between a given HBGF and a high-affinity HBGF receptor in a cell-free sample, which method comprises (a) providing a cell-free sample comprising a hybrid molecule comprising a HBGF-binding portion of a naturally-occurring, high-affinity HBGF receptor polypeptide covalently linked to an antigenic moiety;

(b) contacting said cell-free sample with (i) an amount of heparin or heparin-like molecule which is sufficient to induce binding of an HBGF to said hybrid molecule in the absence of said substance, (ii) said substance, and (iii) said given HBGF;

(c) detecting any affinity complex which may have formed among said hybrid molecule, said HBGF, and said heparin or heparin-like molecule; and (d) repeating each of steps (a) through (c) in the absence of said substance, wherein a difference in the amount of said affinity complex formed in the presence of said substance compared to in the absence of said substance is an indication that said substance can affect said interaction.

* * * * *

UNITED STATES PATENT AND TRADEMARK OFFICE
CERTIFICATE OF CORRECTION

PATENT NO. : 5,789,182
DATED : August 4, 1998
INVENTOR(S) : Avner Yayon, David M. Ornitz, Michael Klagsbrun, Philip Leder and John G. Flanagan It is certified that error appears in the above-identified patent and that said Letters Patent is hereby corrected as shown below:

Column 5,
Line 4, replace "Mo/MFR/SV" with -- Mo/mFR/SV --;

Column 7,
Line 40, replace "MBEK" with -- mBEK --;

Column 9,
Line 7, replace "Heyaran" with -- Heparin --;
Line 47, replace "MBEK" with -- mBEK --;
Line 51, replace "hPLG" with -- hFLG --;

Column 12,
Line 7, replace "JP2257" with -- JO2257 --;

Column 24,
Line 21, replace "claim 20" with -- claim 22 --.

Signed and Sealed this

Fourteenth Day of May, 2002

*Attest:*

JAMES E. ROGAN
*Attesting Officer*  *Director of the United States Patent and Trademark Office*